(12) United States Patent
Borhan et al.

(10) Patent No.: US 6,787,671 B2
(45) Date of Patent: Sep. 7, 2004

(54) CATALYTIC OSMIUM-ASSISTED OXIDATIVE CLEAVAGE OF OLEFINS

(75) Inventors: Babak Borhan, East Lansing, MI (US); Benjamin R. Travis, Lansing, MI (US); Jennifer M. Schomaker, Mt. Pleasant, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 10/341,499

(22) Filed: Jan. 13, 2003

(65) Prior Publication Data

US 2003/0149299 A1 Aug. 7, 2003

Related U.S. Application Data

(60) Provisional application No. 60/348,699, filed on Jan. 15, 2002.

(51) Int. Cl.$^7$ .......................... C07C 45/00; C07C 27/10; C07C 67/36
(52) U.S. Cl. ....................... 568/314; 568/317; 568/356; 568/398; 568/430; 568/435; 568/485; 562/512.2; 562/521; 562/531; 562/535; 560/114; 560/115; 560/207; 560/210
(58) Field of Search .................................. 568/314, 317, 568/356, 398, 430, 435, 485; 562/512.2, 521, 531, 535; 560/114, 115, 207, 210

(56) References Cited

U.S. PATENT DOCUMENTS

| 3,946,065 A | 3/1976 | Matsui et al. |
| 5,302,589 A | 4/1994 | Frye et al. |
| 5,438,118 A | 8/1995 | Callahan et al. |

OTHER PUBLICATIONS

Arney et al., J. Org. Chem. 58: 6126–6128 (1993).
Lee et al., J. Org. Chem. 44: 2726–2730 (1979).
Gupta et al., J. Chem. Soc.–Perkin Trans. 1: 2970–2973 (1981).
Schmid et al., J. Org. Chem. 56: 4056–4058 (1991).
Price et al., J. Am. Chem. Soc. 64: 552–554 (1942).
Hon et al., Tetrahedron Lett. 34: 6591–6594 (1993).
Schreiber et al., Tetrahedron Lett. 23: 3867–3870 (1982).
Schreiber et al., J. Am. Chem. Soc. 110: 6210–6218 (1988).
Viski et al., J. Org. Chem. 51: 3213–3214 (1986).
Lee et al., J. Am. Chem. Soc. 105: 3188–3191 (1983).
Harris et al., Tetrahedron Lett. 38: 981–984 (1997).
Ferreira et al., J. Org. Chem. 52: 3698–3699 (1987).
Clark et al., J. Chem. Soc.–Chem. Commun., 635–636 (1982).
Noureldin et al., Tetrahedron Lett. 22: 4889–4890 (1981).
Lee et al., J. Org. Chem. 58: 2918–2919 (1993).
Santaniello et al., Tetrahedron Lett. 21: 2655–2656 (1980).
Keck et al., Tetrahedron Lett. 19: 4763–4766 (1978).
Daumas et al., Synthesis, 64–65 (1989).
Cainelli et al., Synthesis, 47–48 (1989).
Shroder, Chem. Rev. 80: 187–213 (1980).
Gobel et al., Angew. Chem.–Intl. Ed. Engl. 32: 1329–1331 (1993).
Ogino et al., Tetrahedron Lett. 32: 3965–3968 (1991).
Milas et al., J. Am. Chem. Soc. 81: 4730–4733 (1959).
Sharpless et al., J. Am. Chem. Soc. 98: 1986–1987 (1976).
Ogle et al., Process Saf. Prog. 17: 127–133 (1998).
Gershenzon et al., High Energy Chem. 11: 218–222 (1977).
Travis and Borhan, Tetrahedron Letts. 42: 7741–7745 (2001).
Trost et al., Tetrahedron Lett. 22: 1287–1290 (1981).
Davis et al., J. Org. Chem. 53: 5004–5007 (1988).
Wozniak et al., Tetrahedron Lett. 40: 2637–2640 (1999).
Brik, Tetrahedron Lett. 36: 5519 (1995).
Webb et al., Tetrahedron 54: 401–410 (1998).
Baumstark et al., Tetrahedron Lett. 30: 5567–5570 (1989).
Kobayashi et al., Org. Lett. 3: 2649–2652 (2001).
Jacobsen et al., J. Am Oil Chem. Soc. 71: 653–655 (1994).
Mhaskar et al., J. Am. Oil Chem. Soc. 71: 543–544 (1994).
Kula et al., J. Am. Oil Chem. Soc. 71: 545–546 (1994).
Rebrovic, J. Am. Oil Chem. Soc. 69: 159–165 (1992).
Bunce et al., Org. Prep. Proced. Int. 19: 67–71 (1987).
Karim et al., Org. Prep. Proced. Int. 22: 648–650 (1990).
McMurry et al., J. Org. Chem. 43: 3255–3266 (1978).
Macaulay, J. Org. Chem. 45: 734–735 (1980).
Bressan et al., J. Molec. Catal. 79: 85–93 (1993).
Bolm et al., Org. Lett. 2: 1173–1175 (2000).
Hajipour et al., Chem. Lett. 460–461 (2000).
Hirano et al., Bull. Chem. Soc. Jpn. 64: 1046–1047 (1991).

Primary Examiner—Johann Richter
Assistant Examiner—Sikarl A. Witherspoon
(74) Attorney, Agent, or Firm—Ian C. McLeod

(57) ABSTRACT

An osmium-assisted process for the oxidative cleavage of oxidizable organic compounds such as unsaturated organic compounds, including alkenes and olefins into aldehydes, carboxylic acids, esters, or ketones. The process uses a metal catalyst comprising osmium and a peroxy compound selected from the group consisting of peroxymonosulfuric acid and salts thereof to oxidatively cleave the oxidizable organic compound. In particular, the process enables aldehydes, carboxylic acids, esters, or ketones to be selectively produced from the corresponding mono-, 1,1-di-, 1,2-di-, tri-, or tetra-substituted olefins in a reaction that produces the result of ozonolysis but with fewer problems. The present invention further provides a process for oxidizing an aldehyde alone or with the osmium in an interactive solvent to produce an ester or carboxylic acid.

27 Claims, 13 Drawing Sheets

Scheme 1

Scheme 2

Scheme 3

Scheme 4

Scheme 5

| Solvent | R | Yield |
|---------|-----|-------|
| MeOH | Me | 96 % |
| EtOH | Et | 90 % |
| n-PrOH | n-Pr | 94 % |
| i-PrOH | i-Pr | 95 % |
| t-BuOH | H | 98 % |

FIGURE 4

Scheme 7

Scheme 8

CATALYTIC OSMIUM-ASSISTED OXIDATIVE CLEAVAGE OF OLEFINS

CROSS-REFERENCE TO RELATED APPLICATION

This application claims the benefit of Provisional Application Serial No. 60/348,699 filed Jan. 15, 2002.

STATEMENT REGARDING FEDERALLY SPONSORED RESEARCH OR DEVELOPMENT

Not Applicable.
Reference to a "Computer Listing Appendix submitted on a Compact Disc"
Not Applicable.

BACKGROUND OF THE INVENTION

(1) Field of the Invention

The present invention relates to an osmium-assisted process for the oxidative cleavage of oxidizable organic compounds such as unsaturated organic compounds, including alkenes and olefins into aldehydes, carboxylic acids, esters, or ketones. The process uses a metal catalyst comprising osmium and a peroxy compound selected from the group consisting of peroxymonosulfuric acid and salts thereof to oxidatively cleave the oxidizable organic compound. In particular, the process enables aldehydes, carboxylic acids, esters, or ketones to be selectively produced from the corresponding mono-, 1,1-di-, 1,2-di-, tri-, or tetra-substituted olefins in a reaction that produces the result of ozonolysis but with fewer problems. The present invention further provides a process for oxidizing an aldehyde alone or with the osmium in an interactive solvent to produce an ester or carboxylic acid.

(2) Description of Related Art

In organic synthesis, oxidations and reductions are the key reactions for organic chemists. In particular, oxidative processes are essential components to the success of organic synthesis. Such processes include (1) metal assisted oxidative cleavage of alkenes (potassium permanganate) (Arney et al,. J. Org. Chem. 58: 6126_6128 (1993); Lee et al., J. Org. Chem. 44: 2726_2730 (1979)), (2) oxidative cleavage of diols (sodium periodate) (Gupta et al., J. Chem. Soc._Perkin Trans. 1: 2970_2973 (1981); Schmid et al., J. Org. Chem. 56: 4056_4058 (1991); Price et al., J. Am. Chem. Soc. 64: 552_554 (1942)), and (3) ozonolysis (Hon et al., Tetrahedron Lett. 34: 6591_6594 (1993); Schreiber et al., Tetrahedron Lett. 23: 3867_3870 (1982); Schreiber et al., J. Am. Chem. Soc. 110: 6210_6218 (1988)).

While numerous oxidative and reductive processes have been reported in the prior art, when it comes to cleaving or oxidizing carbon—carbon double bonds in oxidizable organic compounds to form aldehydes, ketones, carboxylic acids, or esters, there are two primary processes for cleaving the organic compounds, either (i) transform the organic compound into a 1,2-diol followed by cleavage with $NaIO_4$ or similar oxidant, or (ii) ozonolysis which transforms the organic compound into a variety of symmetrically or desymmetrically functionalized products depending on the workup conditions.

There are processes for oxidatively cleaving olefins such as oxidative cleavage of diols and ozonolysis, however, while these processes have specific advantages, they also have serious drawbacks. For example, potassium permanganate (KMnO4) is a cheap and useful oxidant, but is not soluble in many organic solvents and it is often non_specific, which means that undesired oxidations occur during the oxidation which makes the workup tedious (Viski et al., J. Org. Chem. 51: 3213_3214 (1986)). In particular, permanganate is not a selective oxidant; thus, there are many possible side reactions in processes that use KMnO4 (Lee et al., J. Am. Chem. Soc. 105: 3188_3191 (1983)). Therefore, much of the work in the area of oxidative cleavage of alkenes using permanganate has been focused on the use of various phase transfer catalysts and solid supported reagents (Harris et al., Tetrahedron Lett. 38: 981_984 (1997); Ferreira et al., J. Org. Chem. 52: 3698_3699 (1987); Clark et al., J. Chem. Soc._Chem. Commun., 635_636 (1982); Noureldin et al., Tetrahedron Lett. 22: 4889_4890 (1981); Lee et al., J. Org. Chem. 58: 2918_2919 (1993)) to modify the reactivity and selectivity of the permanganate, but while these reactions are milder and more selective than permanganate itself, this has not proved to be a general solution to the problem.

Sodium periodate ($NaIO_4$) is another useful reagent for cleaving diols. This reagent is also limited by its insolubility in organic solvents (Schmid et al., J. Org. Chem. 56: 4056_4058 (1991)). To increase the solubility and reactivity of the oxidant, processes have been developed that use quaternary alkyl ammonium periodate (Santaniello et al., Tetrahedron Lett. 21: 2655_2656 (1980); Keck et al., Tetrahedron Lett. 78: 4763_4766 (1978)), potassium metaperiodate along with phase transfer catalysts (Kalsi et al., Chem. Ind., 394_395 (1987)), and silica gel supported $NaIO_4$ (Daumas et al., Synthesis, 64_65 (1989)). While these modifications have to some extent been successful, the primary drawback of these modified reactions is that it is necessary to convert the carbon double bond to a diol before it can be cleaved. As an alternative, catalytic osmium tetroxide ($OsO_4$) and $NaIO_4$ have been used together to oxidatively cleave olefins in a one pot process (Cainelli et al., Synthesis, 47_48 (1989)). However, this reaction often produces undesirable byproducts. To reduce the production of undesirable byproducts, the diol precursor is prepared in a separate reaction which is then used in a second periodate cleavage reaction to produce the cleavage product. Therefore, the process is still a two step process instead of the more desirable one pot process. Furthermore, other 1,2_diols within target molecules needs to be protected from oxidative cleavage.

The over-oxidation pathway, providing α-hydroxy ketones, aldehydes, and carboxylic acids, is seldom described in literature for osmium tetroxide without the use of $NaIO_4$. $OsO_4$ is much better known for formation of 1,2-diols (Shroder, Chem. Rev. 80: 187–213 (1980); Gobel et al., Angew. Chem.-Intl. Ed. Engl. 32: 1329–1331 (1993); Ogino et al., Tetrahedron Lett. 32: 3965–3968 (1991)) by hydrolysis of an intermediate osmate ester. Classically, conditions that usually promote higher levels of over-oxidation include catalytic $OsO_4$ with hydrogen peroxide (Milas et al., J. Am. Chem. Soc. 81: 4730–4733 (1959)) or tert-butyl hydrogen peroxide (Sharpless et al., J. Am. Chem. Soc. 22: 1287–1290 (1976)) as co-oxidants.

U.S. Pat. No. 3,946,065 to Matsui et al. discloses that a combination agent such as osmium tetroxide-sodium periodate or potassium permanganate-sodium periodate can be used to oxidize bicycloheptene to bicyclopentane. Also disclosed is a two-step process for cleaving the double bond of bicycloheptene by oxidizing the double bond to a vicinal alcohol using osmium tetroxide or peracid and then oxidizing the resulting single carbon bond with periodic acid or its metal salts, lead tetraacetate, a manganese compound, or a chromium compound.

In the prior art, the standard process for oxidative cleavage of olefins is ozonolysis. This reaction has been well developed and yields aldehydes or carboxylic acids upon reductive or oxidative workup, respectively (Schreiber et al., Tetrahedron Lett. 23: 3867_3870 (1982)). Desymmetrization of the carbonyl functionality upon cleavage of cyclic olefins is also possible through the use of interactive solvents that yield an ester and an aldehyde (Hon et al., Tetrahedron Lett. 34: 6591_6594 (1993); Schreiber et al., J. Am. Chem. Soc.110: 6210_6218 (1988)).

Ozonolysis is a unique reaction that enables the cleavage of double-bonded carbons with ozone to yield aldehydes, carboxylic acids, or esters, which are then used as starting materials for producing a variety of important organic compounds. Ozonolysis is used by the petroleum industry to process crude oil into many small pure organic molecules, which are then used to make a variety of petrochemical products. While ozonolysis of crude oil is the primary commercial process for producing these important organic compounds, many of the ozonolysis reactions are low yielding. Furthermore, ozonolysis is an inherently dangerous process. The ozonides produced during ozonolysis are particularly dangerous and pose the risk of explosion. Therefore, an alternative reaction that is able to perform in a manner similar to ozonolysis would be highly desirable.

As important as ozonolysis has proved to be in synthetic chemistry, there are no alternative reactions that duplicate the same transformation. Therefore, in reactions where the conditions in which the ozonolysis is to be performed are not tolerated by the olefin, the choice for cleaving the olefin is usually by oxidation of 1,2_diols. A significant problem with ozonolysis is safety. Ozonides generated during ozonolysis are particularly dangerous and serious accidents due to explosions have been reported (Ogle et al., Process Saf. Prog. 17: 127_133 (1998); Koike et al., Chem. Eng. Jpn. 32: 295_299 (1999); Dorofeev et al., Doklady Akademii NauK SSSR 257: 592_596 (1981); Gershenzon et al., High Energy Chem. 11: 218_222 (1977); Gershenzon et al., Kinet. Catal. 18: 1284_1287 (1977)). Therefore, there is a need for a process for cleaving olefins that uses a reaction that produces the results of ozonolysis but without the drawbacks associated with ozonolysis.

SUMMARY OF THE INVENTION

The present invention provides a process for producing carboxylic acids, ketones, or esters from olefins in an osmium-assisted reaction that produces the result of ozonolysis but without the problems associated with ozonolysis. The process is both efficient and inexpensive. The primary elements that make the process of the present invention more advantageous than the processes of the prior art is that (i) the diol intermediate is no longer formed as with the alternative metal-assisted cleavage methodologies, (ii) the process does not require an elaborate setup such as is required for the production of ozone to be used in the ozonolysis, (iii) the reaction is mild and can be performed under a variety of conditions, and (iv) the intermediates formed during the reaction do not pose the risk of explosion. Unexpectedly, it was discovered that the process was versatile in terms of both the oxidation state of the organic compound produced and the functional groups of the substrate that are tolerated.

Therefore, the present invention provides an osmium-assisted process for the oxidative cleavage of oxidizable organic compounds such as unsaturated organic compounds, including alkenes and olefins into aldehydes, carboxylic acids, esters, or ketones. The process uses a metal catalyst comprising osmium and a peroxy compound selected from the group consisting of peroxymonosulfuric acid and salts thereof to oxidatively cleave the oxidizable organic compound. In particular, the process enables aldehydes, carboxylic acids, esters, or ketones to be selectively produced from the corresponding mono-, 1,1-di-, 1,2-di-, tri-, or tetra-substituted olefins in a reaction that produces the result of ozonolysis but with fewer problems. The present invention further provides a process for oxidizing an aldehyde alone or with the osmium in an interactive solvent to produce an ester or carboxylic acid.

Thus, the present invention provides a process for oxidative cleavage of an oxidizable organic compound to form an oxidized organic compound which comprises reacting the oxidizable organic compound with a mixture of a metal catalyst comprising osmium and a peroxy compound selected from the group consisting of peroxymonosulfuric acid and salts thereof which oxidatively cleaves the oxidizable organic compound to form the oxidized organic compound.

The present invention further provides a process for oxidative cleavage of an oxidizable organic compound to form an oxidized organic compound which comprises reacting the oxidizable organic compound with a mixture of a metal catalyst comprising osmium and an alkali metal monopersulfate which oxidatively cleaves the oxidizable organic compound to form the oxidized organic compound. In a particular embodiment of the process, the alkali metal is potassium. In a further embodiment, the oxidizable organic compound contains unsaturated bonds which are oxidized, in particular, wherein the bonds are double bonds. In a further embodiment, the reaction is performed in a non-oxidizable organic solvent. In a further embodiment, the osmium is selected from the group consisting of osmium tetroxide ($OsO_4$), osmium trichloride ($OsCl_3$), $K_2OsO_4 \cdot 2H_2O$, and mixtures thereof.

Further still, the present invention provides a process for oxidizing a carbon—carbon double bond in an organic compound to produce an organic compound selected from the group consisting of an aldehyde, ketone, carboxylic acid, and ester, comprising (a) providing the organic compound with the carbon—carbon double bond in an organic solvent; (b) reacting the organic compound with the carbon—carbon double bond in the organic solvent with a mixture of a metal catalyst comprising osmium and an oxidizing compound selected from the group consisting of peroxymonosulfuric acid and salts thereof in a reaction wherein the carbon—carbon double bond is oxidized to produce the organic compound selected from the group consisting of an aldehyde, ketone, carboxylic acid, and ester; and (c) recovering the organic compound selected from the group consisting of the aldehyde, ketone, carboxylic acid, and ester from the reaction.

In a further embodiment, the osmium is selected from the group consisting of osmium tetroxide ($OsO_4$), osmium trichloride ($OsCl_3$), $K_2OsO_4 \cdot 2H_2O$, and mixtures thereof. Further still, the metal catalyst is provided in a polymer. In a preferred embodiment, the oxidizing compound is an alkali metal peroxymonosulfate, in particular, wherein the alkali metal peroxymonosulfate is potassium peroxymonosulfate or wherein the oxidizing compound comprises 2 $KHSO_5 \cdot KHSO_4 \cdot K_2SO_4$, known by the trade name OXONE.

In a further embodiment, the organic solvent is selected from the group consisting of dimethyl formamide, dichloromethane, methanol, ethanol, propanol, butanol, N-methyl pyrrolidinone, hexamethyl phosphonamide, pyrrolidinone, dimethyl acetomide, and acetone. The alcohols react with the organic acids to form esters.

In an embodiment further still, the organic compound with the carbon—carbon double bond is an olefin, in particular, wherein the olefin is selected from the group consisting of mono-substituted, 1,1 di-substituted, 1,2 di-substituted, tri-substituted, tetra-substituted olefins, and mixtures thereof.

The present invention also provides a composition for use in oxidizing organic compounds which comprises in admixture (a) a metal catalyst comprising osmium; and (b) a peroxy compound selected from the group consisting of peroxymonosulfuric acid and salts thereof.

In a further embodiment, the peroxy compound is an alkali metal peroxymonosulfate, in particular, wherein the alkali metal is potassium. In a further embodiment, the composition is used in a non-oxidizable organic solvent in the process. In a further embodiment, the osmium is selected from the group consisting of osmium tetroxide, osmium trichloride, $K_2OsO_4*2H_2O$, and mixtures thereof Further still, the present invention provides a composition for use in oxidizing an olefin to an aldehyde, ketone, carboxylic acid, or ester which comprises in admixture (a) a metal catalyst comprising osmium; and (b) an oxidizing compound selected from the group consisting of peroxymonosulfuric acid and salts thereof.

In a further embodiment, the osmium is selected from the group consisting of osmium tetroxide ($OsO_4$), osmium trichloride ($OsCl_3$), $K_2OsO_4*2H_2O$, and mixtures thereof. Further still, the metal catalyst is provided in a polymer.

In a further embodiment, the oxidizing compound is an alkali metal peroxymonosulfate, in particular, wherein the alkali metal peroxymonosulfate is potassium peroxymonosulfate or wherein the oxidizing compound comprises 2 $KHSO_5 \cdot KHSO_4 \cdot K_2SO_4$.

The present invention also provides a kit as a package for use in oxidizing an organic compound which comprises (a) a first container of a metal catalyst comprising osmium; and (b) a second container of a peroxy compound selected from the group consisting of peroxymonosulfuric acid and salts thereof.

In a further embodiment, the peroxy compound is an alkali metal peroxymonosulfate, in particular, wherein the alkali metal is potassium.

In a further embodiment, the first and second containers contain a non-oxidizable solvent.

In a further embodiment, the osmium is selected from the group consisting of osmium tetroxide ($OsO_4$), osmium trichloride ($OsCl_3$), $K_2OsO_4*2H_2O$, and mixtures thereof.

In a further embodiment, the present invention provides a process for producing an ester from an aldehyde comprising (a) providing the aldehyde in an alcohol solvent; (b) reacting the aldehyde and the alcohol solvent with an oxidizing compound selected from the group consisting of peroxymonosulfuric acid and salts thereof alone or with an additional oxidant in a reaction wherein the aldehyde is oxidized and which reacts with the alcohol solvent to form the ester; and (c) recovering the ester from the reaction.

In a further embodiment of the process, the oxidizing compound is an alkali metal peroxymonosulfate, preferably wherein the alkali metal peroxymonosulfate is potassium peroxymonosulfate or wherein the oxidizing compound comprises 2 $KHSO_5 \cdot KHSO_4 \cdot K_2SO_4$. Preferably, the alcohol is a lower alcohol and most preferably, the alcohol is selected from the group consisting of methanol, ethanol, propanol, and butanol; however, numerous other alcohols can be used.

In a further embodiment, the additional oxidant is a metal catalyst comprising osmium, preferably the osmium is selected from the group consisting of osmium tetroxide ($OsO_4$), osmium trichloride (OsCl3), $K_2OsO_4*2H_2O$, and mixtures thereof.

The present invention further provides a process for producing a carboxylic acid from an aldehyde comprising (a) providing the aldehyde in a solvent selected from the group consisting of dimethyl formamide, dichloromethane, methanol, ethanol, propanol, butanol, N-methyl pyrrolidinone, hexamethyl phosphonamide, pyrrolidinone, dimethyl acetomide, and acetone; (b) reacting the aldehyde with an oxidizing compound selected from the group consisting of peroxymonosulfuric acid and salts thereof alone or with an additional oxidant in a reaction wherein the aldehyde is oxidized to the acid; and (c) recovering the acid from the reaction.

Preferably, the oxidizing compound is an alkali metal peroxymonosulfate or a soluble form of OXONE. In particular, wherein the alkali metal peroxymonosulfate is potassium peroxymonosulfate. Most preferably, the oxidizing compound comprises 2 $KHSO_5 \cdot KHSO_4 \cdot K_2SO_4$.

In a further embodiment, the additional oxidant is a metal catalyst comprising osmium, preferably the osmium is selected from the group consisting of osmium tetroxide ($OsO_4$), osmium trichloride ($OsCl_3$), $K_2OsO_4*2H_2O$, and mixtures thereof.

Objects

It is an object of the present invention to provide a process for oxidizing an organic compound to produce an oxidized product in a reaction that produces the results of ozonolysis without having the drawbacks of ozonolysis.

In particular, it is an object of the present invention to provide a process for producing carboxylic acids, ketones, aldehydes, or esters from olefins in a reaction that produces the results of ozonolysis without having the drawbacks of ozonolysis.

It is further an object of the present invention to provide a process for producing esters from aldehydes.

These and other objects of the present invention will become increasingly apparent with reference to the following drawings and preferred embodiments.

DESCRIPTION OF THE DRAWINGS

FIG. 4 shows the yields of the various esters that were produced by reacting various aldehydes with OXONE in methanol. R can be any group including, but not limited to, hydrogen, alkyl, aryl, benzyl, and phenyl.

DETAILED DESCRIPTION OF THE INVENTION

Figure 1:
FIG. 1 shows Schemes 1–5 for the selective oxidative cleavage of olefins providing carboxylic acids using $OsO_4$ and OXONE in dimethyl formamide (DMF). $R_1$, $R_2$, $R_3$, and $R_4$ can be any group including, but not limited to, hydrogen, alkyl, aryl, benzyl, and phenyl.
Figure 1:
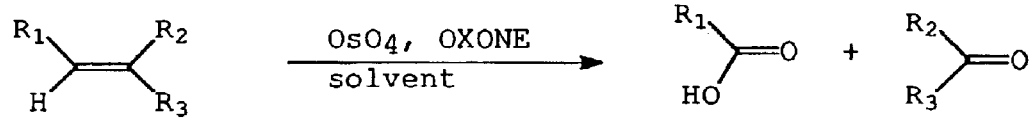
Figure 1:
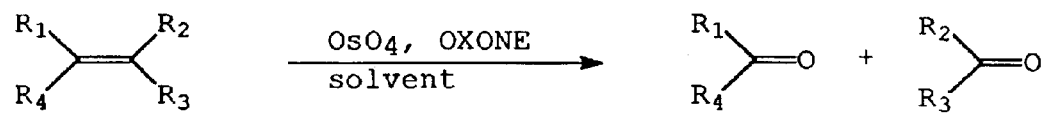
Figure 1:
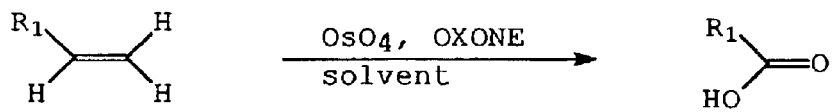
Figure 1:
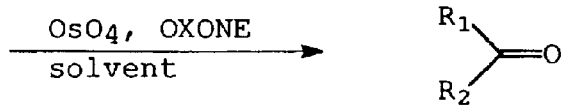

All patents, patent applications, government publications, government regulations, and literature references cited in this specification are hereby incorporated herein by reference in their entirety. In case of conflict, the present description, including definitions, will control.

Earlier work by the inventors in the area of oxidative cyclization of 1,4-dienes in dimethyl formamide (DMF) led to the development of the process of the present invention for cleaving the carbon double bonds of olefins (Travis and Borhan, Tetrahedron Letts. 42: 7741–7745 (2001)). In the osmium-catalyzed oxidative cyclization reactions of 1,4-dienes in DMF, it was observed that a substantial amount of over-oxidized products which had been produced by oxidative cleavage of the olefin functionalities on the 1,4-dienes. Attempts to optimize the yield of the cyclized product by adding a co-oxidant to the osmium-catalyzed reactions did not improve the yield of the cyclized product. Instead, increased levels of over-oxidized product were produced, primarily carboxylic acids. Therefore, as a result of the attempt to improve the yield of the cyclized product from olefins an improved process was discovered for oxidative cleavage of olefins to produce carboxylic acids, ketones, and esters in a reaction that produces the result of ozonolysis but with comparable product yields and without producing the explosive side products that are produced during ozonolysis.

Thus, the present invention provides a process that in one embodiment provides an oxidative cleavage reaction that produces the result of ozonolysis. The process of the present invention uses a metal catalyst such as osmium tetroxide ($OsO_4$) and an oxidizing or peroxy compound selected from the group consisting of peroxymonosulfuric acid and salts thereof in a reaction that oxidizes an oxidizable organic compound, preferably an unsaturated organic compound, to form an oxidized organic compound. In particular, the present invention provides a process for oxidizing a carbon—carbon double bond in an oxidizable organic compound to produce an organic compound selected from the group consisting of aldehyde, ketone, carboxylic acid, or ester. Further, in a preferred embodiment, the present invention provides a process for oxidizing a carbon—carbon double bond in an olefin to produce an organic compound selected from the group consisting of aldehyde, ketone, carboxylic acid, or ester. Preferably, the oxidizing compound is an alkali metal peroxymonosulfate, preferably potassium peroxymonosulfate, and most preferably, the oxidizing compound comprises 2 $KHSO_5 \cdot KHSO_4 \cdot K_2SO_4$. Thus, in the preferred embodiment, the process of the present invention provides a means for selectively producing aldehydes, ketones, carboxylic acids, and esters from the corresponding mono-substituted, 1,1 di-substituted, 1,2 di-substituted, tri-substituted, or tetra-substituted olefins.

Unsaturated organic compounds contain one or more carbon—carbon double bonds or carbon—carbon—carbon triple bonds which includes olefins and variants, and alkenes. Olefins are unsaturated hydrocarbons of the type $C_nH_{2n}$. Olefin variants include olefin acids ($C_nH_{2n-1}COOH$), olefin alcohols ($C_nH_{2n-1}OH$), olefin aldehydes ($C_nH_{2n-1}CHO$), and olefin ketones ($C_nH_{2n}CO$) As used herein, "olefin" is to be understood to include the olefin variants and substituted olefins and olefin variants. Alkenes are aliphatic unsaturated hydrocarbons of the type $C_nH_{2n}$. As used herein, "alkenes" is to be understood to include substituted alkenes. Wherever the term "oxidizable organic compound" is used herein, it is to be understood that the term includes olefins and alkenes. Also, wherever "olefin" or "alkene" is used herein, it is to be understood that the "oxidizable organic compound contains one or more carbon—carbon double bonds," or the equivalent, which can be substituted with O, N, S, P, and many other groups.

The oxidizing compound is an alkali metal peroxymonosulfate, preferably potassium peroxymonosulfate, and most preferably, the oxidizing compound comprises the triple salt 2 $KHSO_5 \cdot KHSO_4 \cdot K_2SO_4$ (potassium hydrogen peroxymonosulfate sulfate, CAS-RN 70693-62-8) of which potassium peroxymonosulfate or potassium monopersulfate salt ($K^{+13}$ O—S(=O)$_2$(—OOH) or $KHSO_5$), CAS-RN 10058-23-8 or 10361-76-9) is the active ingredient. $KHSO_5$ structurally resembles hydrogen peroxide or tert-butyl hydrogen peroxide. Potassium hydrogen peroxymonosulfate sulfate is commonly sold under the trademark OXONE (the trademark OXONE is owned by E. I. du Pont de Nemours and Company, Wilmington, Del.). OXONE is well known to enable sulfones or sulfoxides to be prepared from sulfides (Trost et al., Tetrahedron Lett. 22: 1287–1290 (1981); Davis et al., J. Org. Chem. 53: 5004–5007 (1988)), oxides of both phosphorous (Wozniak et al., Tetrahedron Lett. 40: 2637–2640 (1999)) and nitrogen (Brik, Tetrahedron Lett. 36: 5519 (1995)), and several reports have shown that OXONE can also be used to oxidize aldehydes to carboxylic acids (Webb et al., Tetrahedron Lett. 54: 401–410 (1998); Baumstark et al., Tetrahedron Lett. 30: 5567–5570 (1989)). There are equivalents of OXONE such as potassium hydrogen peroxymonosulfate (CAS-RN 37222-66-5) available from Sigma, St. Louis, Mo., which can be used in the process of the present invention. The present invention embraces any alkali metal monopersulfate, in particular, wherein the metal is potassium, or to any peroxy compound selected from the group consisting of peroxymonosulfuric acid and salts thereof.

Figure 2:
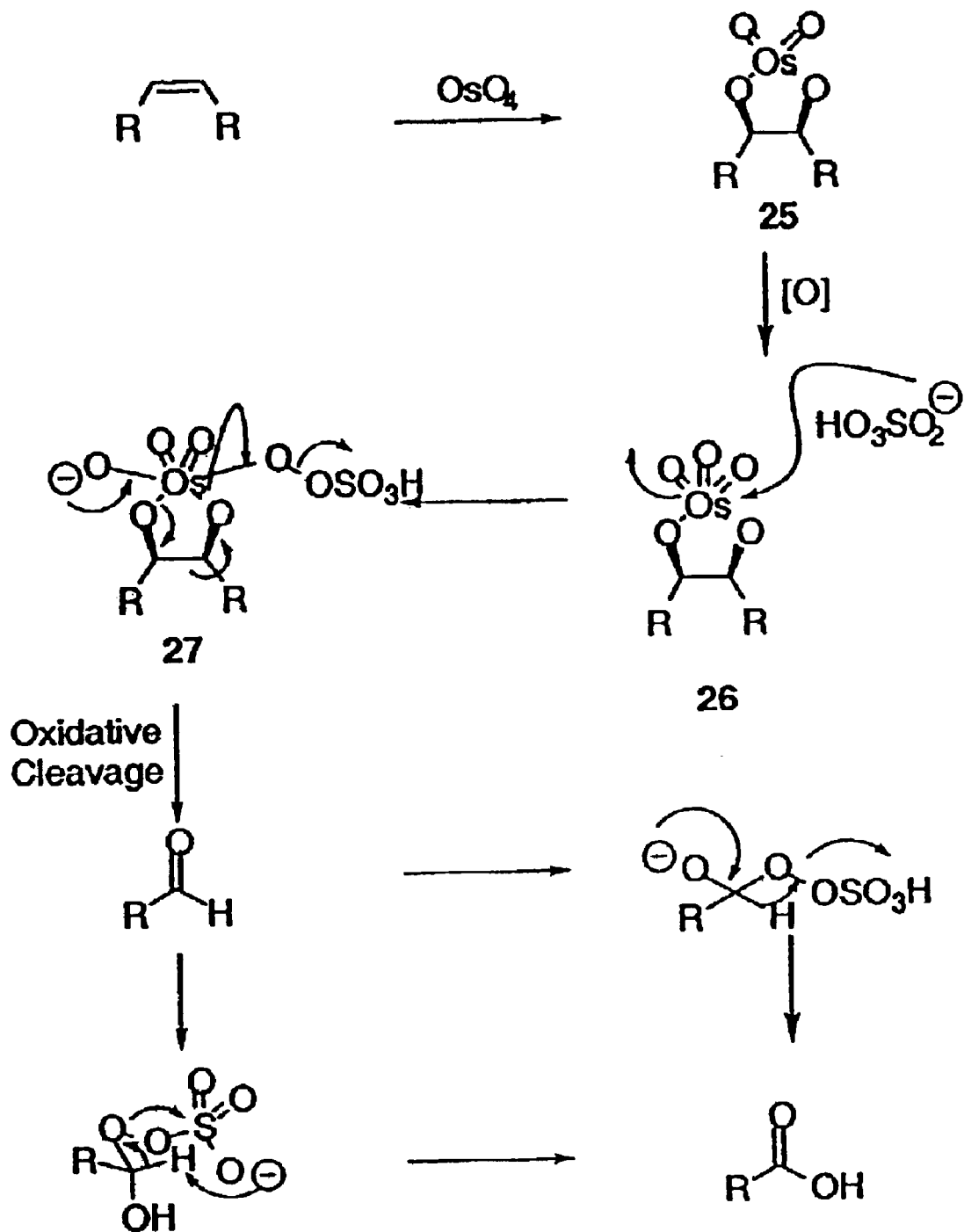
FIG. 2 shows Scheme 6 which is an illustration of a possible mechanism for the oxidative cleavage of an olefin to produce the carboxylic acid in a reaction catalyzed by $OsO_4$ in dimethyl formamide containing OXONE. R can be any group including, but not limited to, hydrogen, alkyl, aryl, benzyl, and phenyl. The OXONE also participates in the reaction in a way which is not understood.

The mechanism of the oxidative cleavage in the process of the present invention has not been determined with certainty; however, it appears that during the reaction, the olefin and the osmium tetroxide form an osmate ester intermediate which undergoes the oxidative cleavage. It does not appear that the 1,2-diol is an intermediate of this reaction for two reasons, (i) the oxidation of olefins with the $OsO_4$/OXONE mixture of the present invention proceeds just as well under anhydrous conditions, i.e, there is no hydrolysis of the osmate ester intermediate, and (ii) the submission of 1,2-diols to this reaction does not yield products, and in fact, the starting 1,2-diols are recovered quantitatively. Scheme 6 shown in FIG. 2 depicts a possible mechanism for the reaction in which the osmate ester intermediate (25) is oxidized by OXONE to form the intermediate (26) which is subsequently attacked by the OXONE to yield intermediate (27). Fragmentation of intermediate (27) regenerates $OsO_4$ and produces two aldehyde intermediates which in the presence of the OXONE are independently oxidized to yield carboxylic acids through a proposed Baeyer-Villiger oxidation as shown in Scheme 2 (FIG. 2) or ketones or esters. During the reaction, the OXONE appears to have three distinct oxidizing roles (i) it re-oxidizes osmium (VI) to osmium (VIII), which makes the process catalytic, (ii) it promotes the oxidative cleavage of the substrate to an intermediate aldehyde, and (iii) it independently oxidizes the aldehyde intermediate to the carboxylic acid.

Therefore, in the above embodiment of the process of the present invention, carboxylic acids or ketones are produced by the selective oxidative cleavage of olefins or alkenes using catalytic $OsO_4$ and OXONE in a solvent such as dimethyl formamide (DMF). Schemes 1–5 in FIG. 1 shows the reactions for the production of carboxylic acids or ketones from various olefins or alkenes wherein $R_1$, $R_2$, $R_3$, and $R_4$ can be any group including, but not limited to, hydrogen, alkyl, aryl, benzyl, and phenyl.

As shown in Scheme 1, when each carbon in the double bond of the olefin or alkene has an R group and a hydrogen in either a cis or trans configuration (cis configuration shown), the reaction produces 2 moles of carboxylic acids for every mole of olefin or alkene.

As shown in Scheme 2, when one carbon of the double bond in the olefin or alkene has an R group and a hydrogen and the other carbon has two R groups, the reaction produces one mole of carboxylic acids and one mole of ketones for every mole of olefin or alkene.

As shown in Scheme 3, when each carbon of the double bond of the olefin or alkene contains R groups, the reaction produces two moles of ketones for every mole of olefin or alkene.

As shown in Scheme 4, when one carbon of the double bond of the olefin or alkene contains an R group and a hydrogen and the other carbon contains two hydrogens, the reaction produces one mole of carboxylic acids for every mole of olefin or alkene.

As shown in Scheme 5, when one carbon of the double bond of the olefin or alkene contains two R groups and the other carbon contains two hydrogens, the reaction produces one mole of ketones for every mole of olefin or alkene.

In general, the preparation of ketones and carboxylic acids from substituted olefins is performed as follows. About 1 equivalent (eq.) of the olefin is dissolved in dimethyl formamide (DMF). The DMF can range in concentration from 0.01 to 1 M, but preferably the DMF is 0.2 M. Next, about 0.01 to 0.05 eq. of the $OsO_4$ (provided as a 2.5% solution in tBuOH) is added and the mixture mixed for a brief period of time (usually five minutes is sufficient). Then, 2 to 4 eq. of the OXONE is added to provide the reaction solution. The reaction solution is incubated at room temperature with constant stirring for about 3 hours or until the reaction solution becomes colorless. However, the reactions can be performed from between about −30° C. to about 90° C., preferably, between about 0° C. and 50° C. The reactions can be performed at one atmosphere or under pressure. Performing the reactions under pressure has the advantage of allowing the reaction to be performed at temperatures which at one atmosphere would cause the solvent to decompose. Completion of the reaction can be verified by testing aliquots of the reaction by thin-layer chromatography (TLC) or gas chromatography (GC). After the reaction has been completed, about 6 eq. of $Na_2SO_3$ is added to the reaction solution to reduce any remaining Os(VIII) and the solution is stirred for about an hour or until the solution turns dark brown or black. The reaction products are extracted in an organic solvent such as EtOAc and the salts dissolved with 1N HCl. The organic extract is washed three times or more with 1N HCl and brine, dried over $Na_2SO_4$. The EtOAc is removed under reduced pressure to produce the crude oxidized product. The crude product can be further purified by silica gel chromatography.

In general, the preparation of aldehydes from substituted olefins is performed as follows. About 1 eq. of the olefin is dissolved in a solvent such as $CH_2Cl_2$ or dimethylformamide. Preferably, the solvent is freshly distilled and is a solution between about 0.01 to 0.5 M, preferably at 0.1 M. One eq. of an additive such as $KHCO_3$, $NaHCO_3$, or methane sulfonamide is then added. Next, about 0.01 to 0.05 eq. of the $OsO_4$ (provided as a 2.5% solution in tBuOH) is added and the mixture mixed for a brief period of time (usually five minutes is sufficient). Then, 2 eq. of OXONE or tetrabutylammoniumperoxysulfate is added to provide the reaction solution. The reaction solution is incubated at room temperature with constant stirring for about 3 hours. However, the reactions can be performed from between about −30° C. to about 90° C., preferably, between about 0° C. and 50° C. The reactions can be performed at one atmosphere or under pressure. Performing the reactions under pressure has the advantage of allowing the reaction to be performed at temperatures which at one atmosphere would cause the solvent to decompose. Completion of the reaction can be verified by testing aliquots of the reaction by TLC or GC. After the reaction has been completed, about 2 eq. of $Na_2SO_3$ is added to the reaction solution to reduce any remaining Os(VIII) and the solution stirred for about an hour or until the solution turns dark brown or black. The solvent is removed under reduced pressure to produce the crude oxidized product. The crude product can be further purified by silica gel chromatography using $MeOH/CH_2Cl_2$.

It was further discovered that a reaction comprising an aldehyde and OXONE in a hydroxyl containing solvent such as methanol, ethanol, isopropanol, or butanol, the aldehyde was converted to an ester. It was further discovered that a reaction comprising an olefin, $OsO_4$, and OXONE in the above interactive solvents, the olefin was converted to an ester. The species of ester, e.g., methyl, ethyl, isopropyl, or butyl, depended on the interactive solvent, e.g., methanol, ethanol, isopropanol, or butanol. Therefore, in another embodiment, the process of the present invention provides a reaction that oxidizes aldehydes to esters.

In a typical reaction to produce an ester from an aldehyde, 1 eq. of aldehyde is dissolved in the interactive solvent which is at about 0.2 M. Next about 1 eq. OXONE is added and the reaction stirred at room temperature for about 18 hours or until complete. However, the reactions can be performed from between about −30° C. to about 90° C., preferably, between about 0° C. and 50° C. The reactions can be performed at one atmosphere or under pressure. Performing the reactions under pressure has the advantage of allowing the reaction to be performed at temperatures which at one atmosphere would cause the solvent to decompose. The reaction is monitored by testing aliquots of the reaction by TLC or GC. When the reaction is judged complete, EtOAc is added to extract the reaction products and 1 N HCl is used to dissolve the salts. The organic extract is washed three times or more with 1N HCl and brine, dried over $Na_2SO_4$. The EtOAc is removed under reduced pressure to produce the crude oxidized product. The crude product can be further purified by silica gel chromatography.

Figure 3:
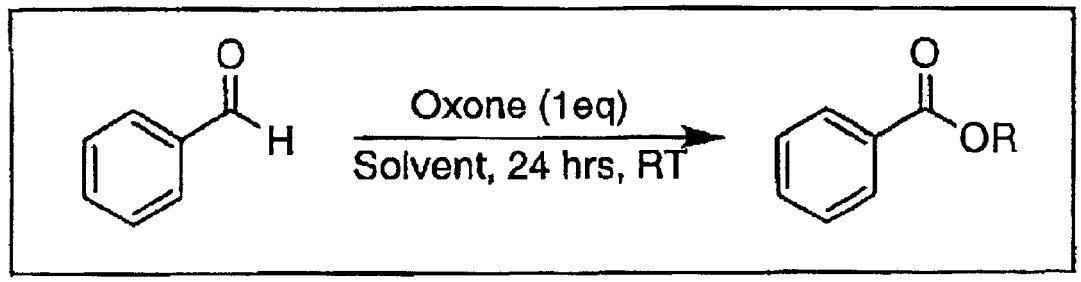
FIG. 3 shows the yields of various esters that were produced by the oxidation of benzaldehyde with OXONE in the interactive solvent methanol, ethanol, n-propanol, i-propanol, or t-butanol.

FIG. 3 shows the oxidation products of benzaldehyde (or benzaldehyde intermediates produced by the $OsO_4$/OXONE) that were produced in a reaction containing OXONE in particular interactive solvents. In a typical reaction starting from a benzaldehyde, the benzaldehyde is incubated in an interactive solvent including, but not limited to, methanol, ethanol, propanol, or butanol containing one eq. of the benzaldehyde, one or more eq. of OXONE for about 24 hours at room temperature. The OXONE in the particular solvent oxidizes the benzaldehyde to the ester in linkage with the group that corresponds to the solvent, e.g., methanol results in a methyl ester, propanol results in a propyl ester, ethanol results in an ethyl ester, and butanol results in a butyl ester.

In a reaction starting from a benzolefin, the benzolefin is incubated in an interactive solvent including, but not limited to, methanol, ethanol, propanol, or butanol containing one eq. of the olefin, two or more eq. of OXONE, and about 0.05 eq. of the $OsO_4$ for about 24 hours at room temperature. The OXONE and $OsO_4$ produce the benzaldehyde intermediate which because of the OXONE in the particular solvent is further converted to the ester, the species of which depends on the interactive solvent. Other benzylesters can be made when other alcohol solvents are used.

Figure 4:
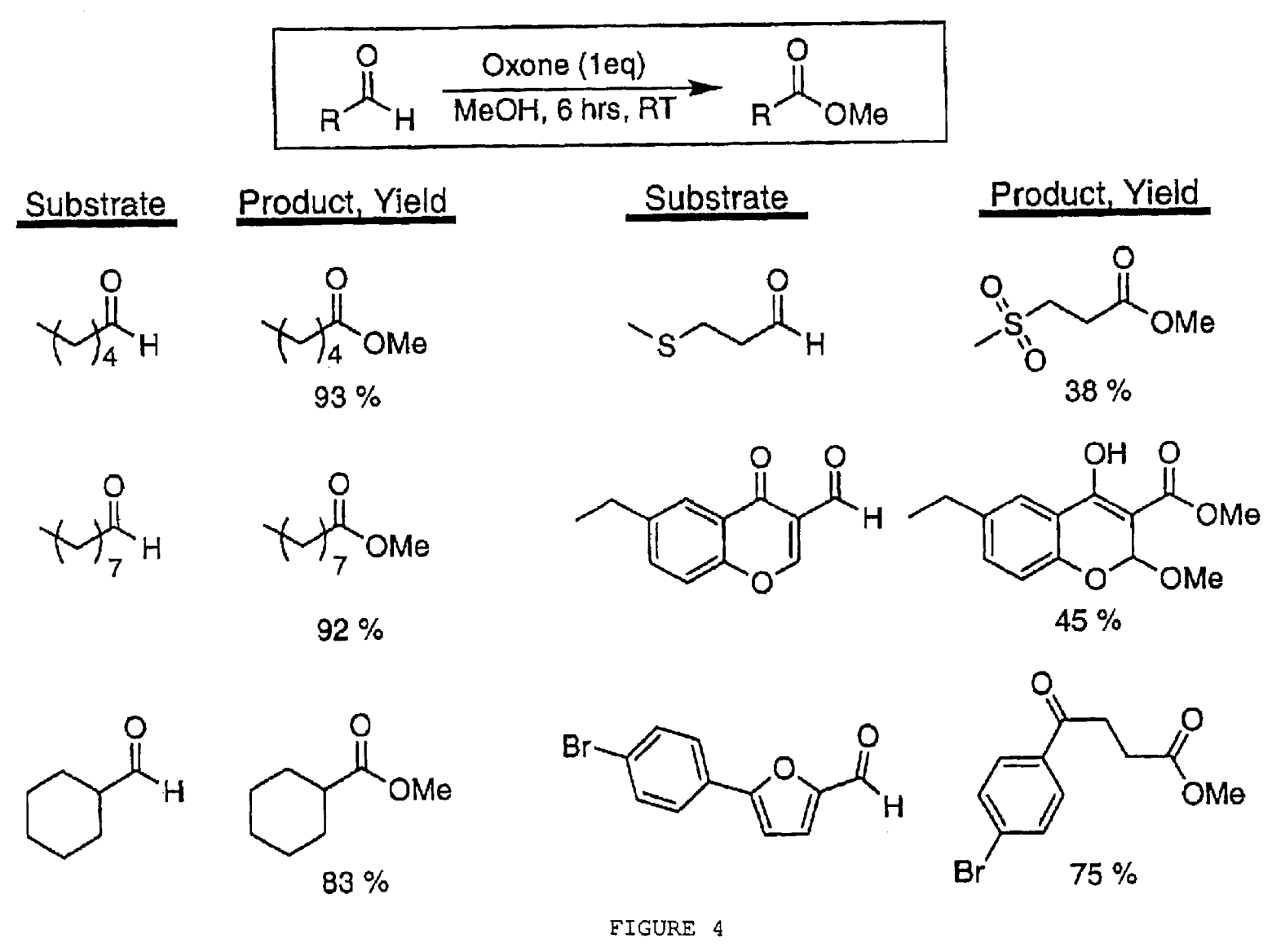
Figure 6:
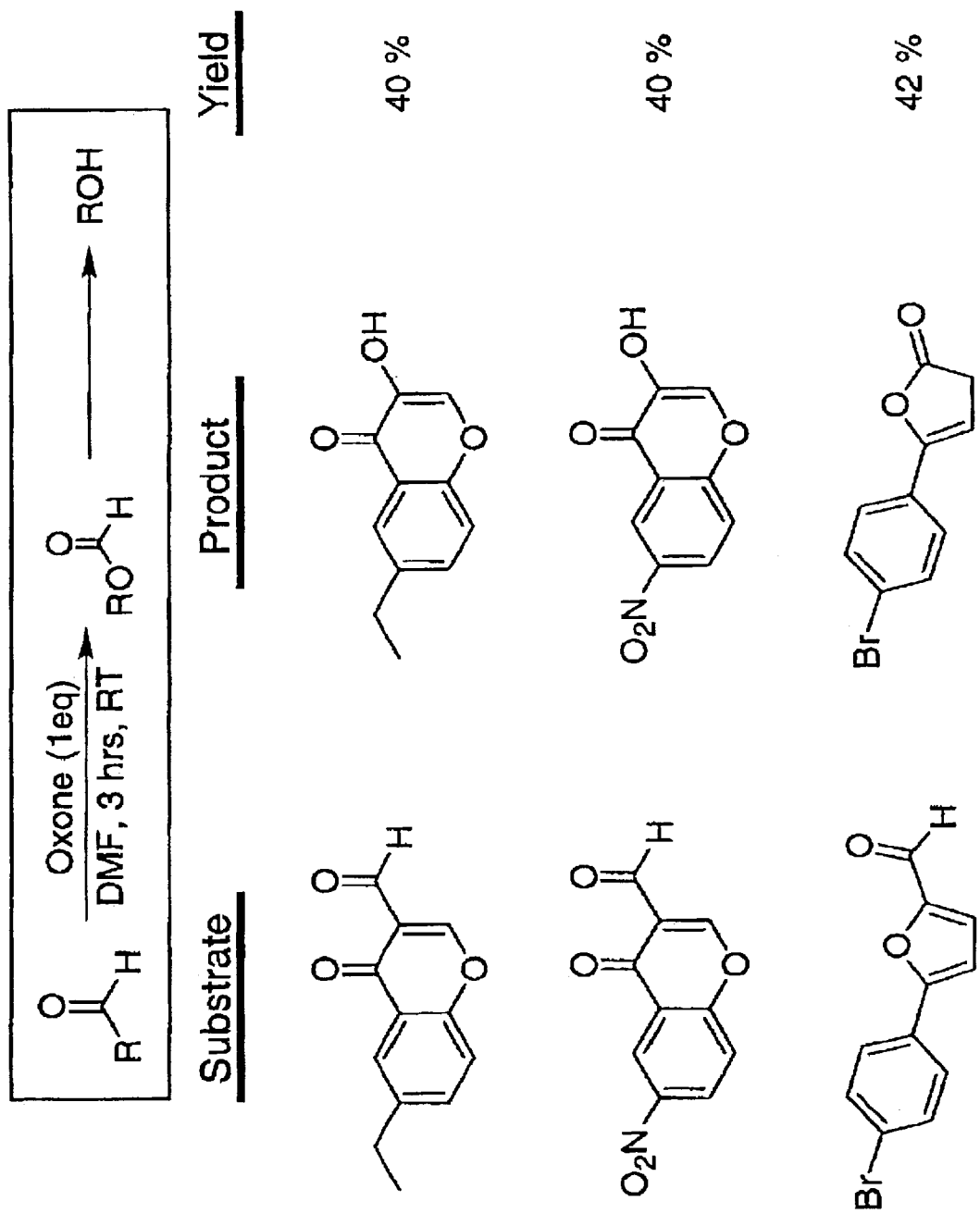
FIG. 6 shows the yields of the oxidation products of various aldehydes that were produced by reacting the aldehydes with OXONE in dimethyl formamide (DMF). R can be any group including, but not limited to, hydrogen, alkyl, aryl, benzyl, and phenyl.

FIG. 4 shows the oxidation products of other aldehydes or aldehyde intermediates in methanol containing OXONE. In a typical reaction starting from the aldehyde, the aldehyde (about one equivalent) was incubated in methanol containing about 1 eq. or more of the OXONE for about six hours at room temperature. The OXONE produced the methyl ester from the aldehyde. In a reaction starting from the olefin, the olefin (about one equivalent) was incubated in methanol containing about two eq. or more of the OXONE and about 0.05 eq. of the $OsO_4$ for about six hours at room temperature. The OXONE and $OsO_4$ produced the aldehyde intermediate which because of the OXONE in methanol was further converted to the methyl ester. Other ester species can be produced by changing the interactive solvent. For example, when the solvent was propanol, a propyl ester was produced, when the solvent was ethanol, an ethyl ester was produced, and when the solvent was butanol, a butyl ester was produced. Other esters can be made when other alcohol solvents are used. FIG. 6 shows examples of the oxidation of other aldehydes to alcohol or ketone products.

While the oxidation of aldehydes to carboxylic acids has been described previously, the oxidation of aldehydes to esters in a reaction containing OXONE and an interactive solvent was unexpected. Therefore, both the $OsO_4$/OXONE reactions that oxidize olefins to carboxylic acids, ketones, or esters (when in an interactive solvent) and OXONE reactions that oxidize aldehydes to esters in interactive solvents are novel. In light of the above, the present invention in one embodiment provides a process for producing carboxylic acids, ketones, aldehydes, and esters from an olefin or alkene and in another embodiment provides a process for producing esters from aldehydes.

Figure 5:
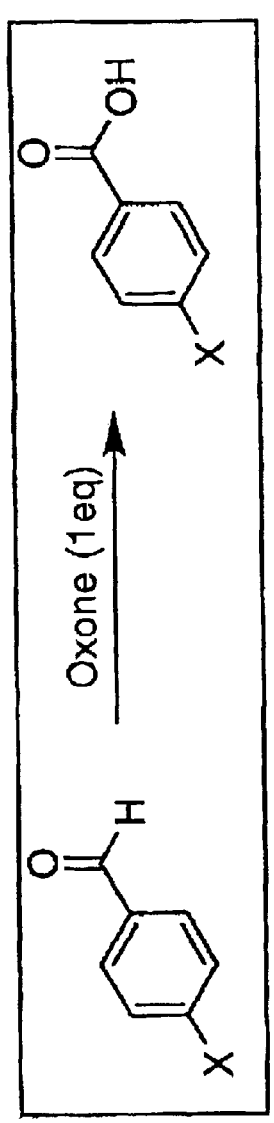
FIG. 5 shows the yields of the oxidation products of aromatic aldehydes with particular groups on the aromatic ring that were produced by reacting the aromatic aldehydes with OXONE in dimethyl formamide (DMF). Electron withdrawing groups form only the acid product whereas electron donating groups preferred to form a mixture of acid and formate ester, the latter in higher yields. "X" is the substrate group on the aromatic aldehyde.

As shown in FIG. 5, when the olefin comprises an aromatic ring with an electron withdrawing group such as $NO_2$, CN, Cl, $CO_2Me$, H, or Me, the product that is formed from the aldehyde in a reaction consisting of the aldehyde in dimethyl formamide containing OXONE is a carboxylic acid. However, when the olefin is an aromatic ring and the group on the ring is an electron donating group such as a hydroxyl or methyl ester, the product that is formed from the aldehyde in a reaction consisting of the aldehyde in dimethyl formamide containing OXONE is a mixture of the carboxylic acid and a formate ester with the latter in higher yield (FIG. 5).

Figure 8:
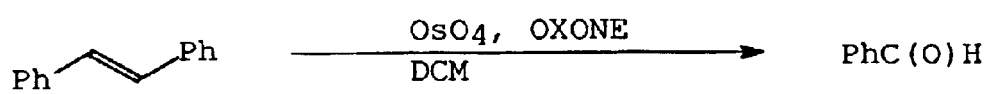
FIG. 8 shows Scheme 7 which illustrates the oxidative cleavage of trans-stilbene to an aldehyde in a reaction containing $OsO_4$ and OXONE in dichloromethane (DCM) and Scheme 8 illustrates the oxidative cleavage of trans-stilbene to a methyl ester in a reaction containing $OsO_4$ and OXONE in methanol.
Figure 8:
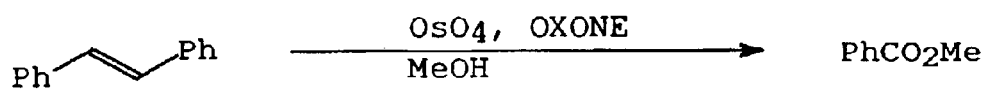
Figure 9A:
FIG. 9a shows the structure of the substrates 9-decenyl acetate (12), (−)-isopulegol (13), and (1R,2S,5R)-(2-isoprenyl-5-methyl-cyclohexyl)benzyl ether (14), and their respective oxidative cleavage products 9-acetoxy nonanoic acid (12a), (1R,2R,5R)-2-acetyl-5-methyl cyclohexanol (13a), (1R,2R,5R)-2-acetyl-5-methyl cyclohexanyl formate (13b), and (1R,2S,5R)-(2-acetyl-5-methyl-cyclohexyl) benzyl ether (14a) which are identified in Table 2.
Figure 9A:
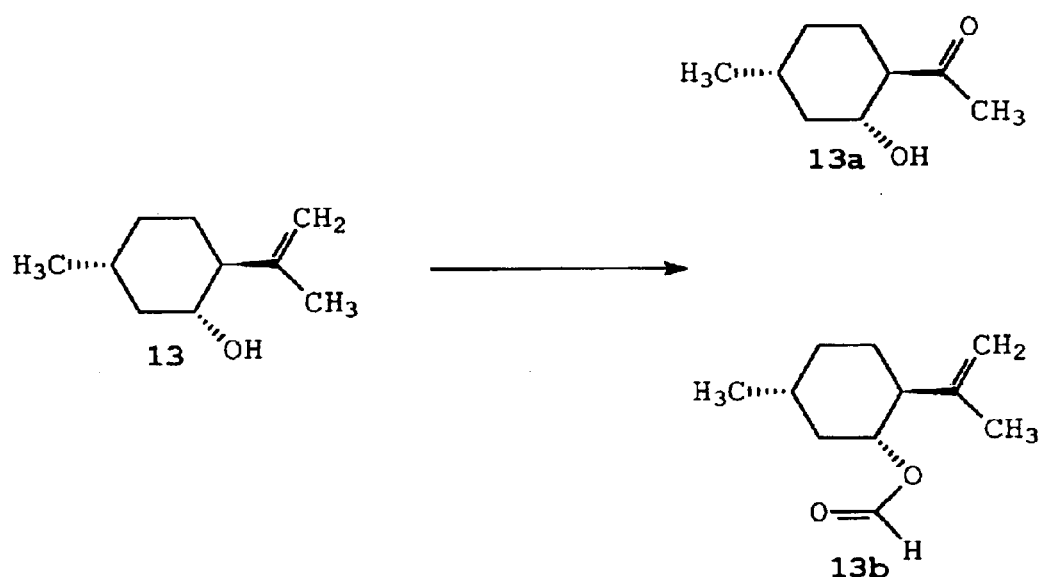
Figure 9A:
Figure 9B:
FIG. 9b shows the structure of the substrates 4,4'-dimethyl stilbene (15), 4,4'-dinitro stilbene (16), and 2-cyclohexeone (17), and their respective oxidative cleavage products 4-methyl benzoic acid (15a), 4-nitro benzoic acid (16a), and glutaric acid (17a) which are identified in Table 2.
Figure 9B:
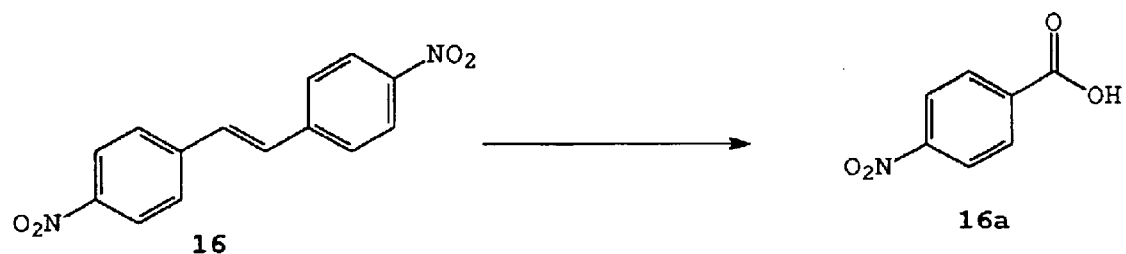
Figure 9B:
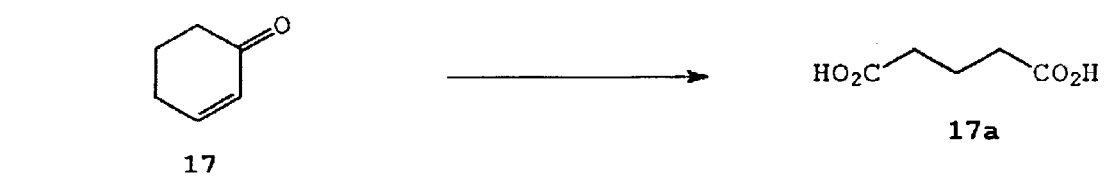
Figure 9C:
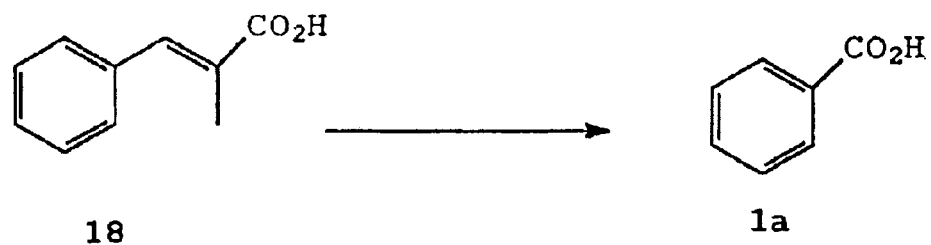
FIG. 9c shows the structure of the substrates α-methyl cinnamic acid (18), methyl cyclohexene (19), and 2,3-diphenyl-2-butene (20), and their respective oxidative cleavage products benzoic acid (1a), 6-oxyheptanoic acid (19a), and acetophenone (20a) which are identified in Table 2.
Figure 9C:
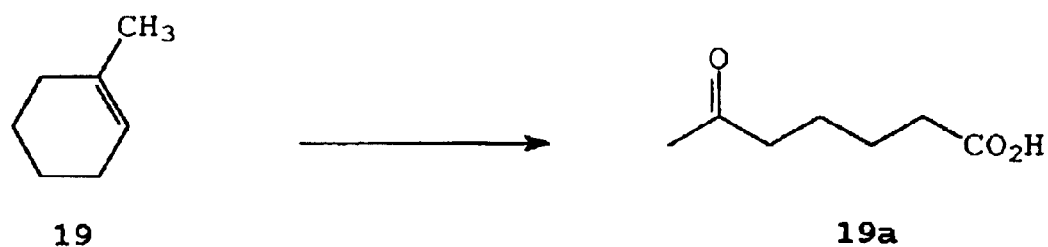
Figure 9C:
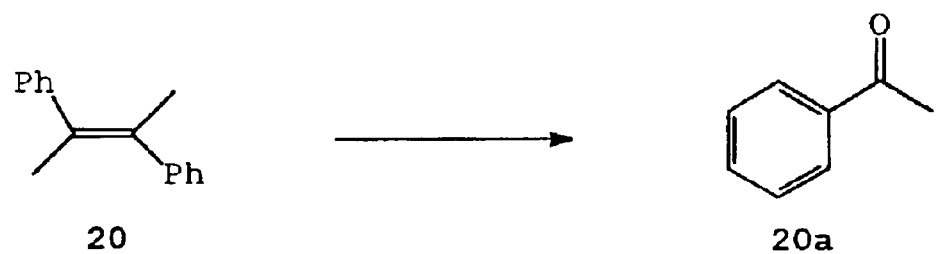
Figure 9D:
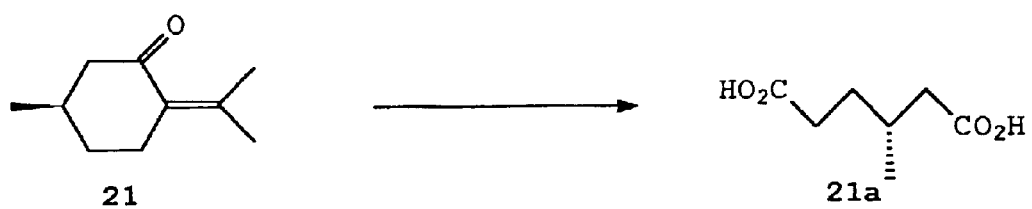
FIG. 9d shows the structure of the substrates (+)-pulegone (21), nootkatone (22), 15-hexadecynyl acetate (23), and careen (24) and their respective oxidative cleavage products 3R-methyladipic acid (21a), (4S,4aR,6R)-6-acetyl-4,4a-dimethyl-4,4a,5,6,7,8-hexahydro-3H-naphthalen-2-one (22a), [2,2-dimethyl-3-(2-oxo-propyl)-cyclopropyl]-acetic acid (24a), 3,7,7-trimethyl-bicyclo[4.1.0]heptane-3,4-diol (24b), and formic acid 4-hydroxy-4,7,7-trimethyl-bicyclo[4.1.0]heptane-3-ylester (24c) which are identified in Table 2.
Figure 9D:
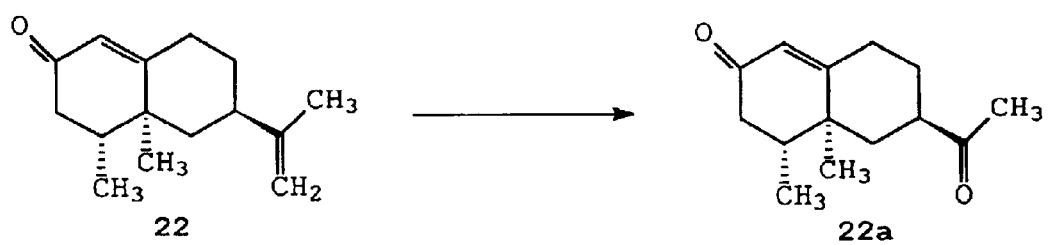
Figure 9D:
Figure 9D:
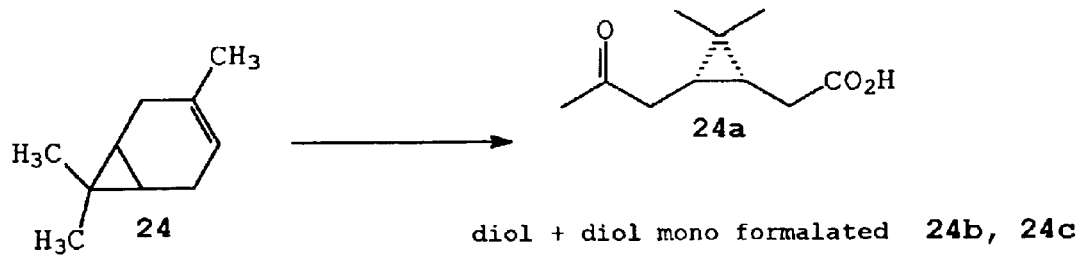

FIG. 8 shows that particular solvents can be used to stop the $OsO_4$/OXONE oxidation at the aldehyde intermediate stage. For example, as shown in Scheme 7 of FIG. 8, the $OsO_4$ catalyzed oxidation of trans-stilbene with OXONE was unexpectedly arrested at the aldehyde stage when the reaction was performed in a solvent such as dichloromethane (DCM). It is clear from the above that the process of the present invention enables particular products to be produced in the $OsO_4$/OXONE and OXONE reactions by changing the solvent the reaction is performed in. Therefore, as shown herein, the process of the present invention is versatile and can be performed in a wide variety of organic solvents including, but not limited to, methanol, ethanol, isopropanol, butanol, acetone, dimethyl formamide, and dichloromethane.

The process of the present invention is an improvement over the ozonolysis process and has several important advantages. First, unlike the ozonolysis process, the process of the present invention provides a mild and versatile system that can tolerate many types of functionalities. For example, changing the solvent that the reaction is performed in is sufficient to determine the oxidation state of the organic compound that is produced, i.e., aldehyde, acid or ester, which is a valuable feature for an organic reaction. Second, unlike processes that use NaIO$_4$, there is no intermediate 1,2_diol that is formed during the reaction. This allows for a wider range of preexisting functionalities on the substrate. Third, the catalyst, OsO$_4$, displays a high degree of turnover, which means that it can be used in very small amounts thereby making the process efficient. Fourth, the oxidant OXONE is very inexpensive (25 Kg/$200), environmentally friendly, and easy to handle. Fifth, the reactions can be performed within a wide range of temperatures (low or high) with no degradation of the catalyst, oxidant, or the products obtained. Finally, OsO$_4$ can be bound to a polymer support which makes the removal of the catalyst after the reaction has been completed simple and easy. A polymer bound OsO$_4$ catalyzes the reaction as efficiently as when it was in solution. Polymer-supported OsO$_4$ catalysts include, but are not limited to, phenoxyethoxymethyl-polystyrene (PEM) microencapsulated osmium tetroxide (Kobayashi et al., Org. Lett. 3: 2649–2652 (2001)) and osmium tetroxide on poly (4-vinylpyridine) (available from Sigma-Aldrich, St. Louis, Mo.).

The present invention can be used to make oxidized chiral products from unsaturated chiral compounds. In particular, the present invention enables chiral aldehydes, carboxylic acids, esters, or ketones to be selectively produced from the corresponding chiral mono-, 1,1-di-, 1,2-di-, tri-, or tetra-substituted olefins in a reaction that produces the result of ozonolysis. The present invention further provides a process for oxidizing a chiral aldehyde with the above peroxy compound in an interactive solvent to produce a chiral ester. The oxidized products are useful intermediates for the synthesis of pharmaceuticals and other useful compounds.

A number of general conditions have been established for performing the oxidative reactions of the present invention. These conditions, which are enumerated below, are not intended to limit the scope of the reactions of the present invention to the particular conditions set forth. The present invention includes variations of the particular conditions set forth below and conditions within the general scope of the present invention.

Condition A is a general procedure for the oxidative cleavage of mono and disubstituted olefins. In Condition A, the olefin (1 eq) is dissolved in DMF (0.2 M), and OsO$_4$ (0.01 eq, 2.5% in tBuOH) is added and the mixture stirred for 5 min. OXONE (4 eq) is added in one portion and the reaction is stirred at room temperature for 3 hours or until the solution becomes colorless. This usually marks the completion of the reaction which can be verified by TLC or GC. Na$_2$SO$_3$ (6 eq. w/w) is added, to reduce the remaining Os(VIII), and stirred for an additional hour or until solution becomes dark brown/black. EtOAc is added to extract the products and 1N HCl is used to dissolve the salts. The organic extract is washed with 1N HCl (3×) and brine, dried over Na$_2$SO$_4$, and the solvent is removed under reduced pressure to obtain the crude product. Products can be further purified by silica gel column chromatography or the like.

Condition B is a general procedure for the oxidative cleavage of tri- and tetra-substituted olefins. In Condition B, the olefin (1 eq) is dissolved in DMF (0.2 M), and OsO$_4$ (0.01 eq, 2.5% in tBuOH) is added and the mixture stirred for 5 min. A solid mixture of OXONE (4 eq) and NaHCO$_3$ (4 eq) is then added in one portion and the reaction is stirred at room temperature for 3 hours or until solution becomes colorless. This usually marks the completion of the reaction which can be verified by TLC or GC. Na$_2$SO$_3$ (6 eq w/w) is added, to reduce the remaining Os(VIII), and stirred for an additional hour or until solution becomes dark brown/black. EtOAc is added to extract the products and 1N HCl is used to dissolve the salts. The organic extract is washed with 1N HCl (3×) and brine, dried over Na$_2$SO$_4$, and the solvent is removed under reduced pressure to obtain the crude product. Products can be further purified by silica gel column chromatography or the like.

Condition C is a general procedure for oxidizing an olefin using K$_2$OsO$_4$*2H$_2$O. In Condition C, the olefin (100 mg) is dissolved in DMF (5 mL), and K$_2$OsO$_4$*2H$_2$O (0.4 mg) is added and the mixture stirred for 5 min. OXONE (1.23 g) is added in one portion. The reaction is stirred at room temperature for 3 hours or until the solution becomes colorless. This usually marks the completion of the reaction which can be verified by TLC or GC. Na$_2$SO$_3$ (540 mg) is added, to reduce the remaining Os(VIII), and stirred for an additional hour or until solution becomes dark brown/black. EtOAc is added to extract the products and 1N HCl is used to dissolve the salts. The organic extract is washed with 1N HCl (30 mL×3) and brine(30 mL), dried over Na$_2$SO$_4$, and the solvent is removed under reduced pressure to obtain the crude product. Products can be further purified by silica gel column chromatography or the like.

Condition D is a general procedure for the oxidation of an olefin using polymer supported OsO$_4$. In Condition D, the olefin (50 mg) is dissolved in DMF (2 mL), and OsO$_4$ (355 mg, 1 wt % on poly(4-vinylpyridine)) is added and the mixture stirred for 5 min. OXONE (0.683 g) is added in one portion. The reaction is stirred at room temperature for 3 hours or until the solution becomes colorless. This usually marks the completion of the reaction which can be verified by TLC or GC. The reaction is filtered and washed with EtOAc. The organic filtrate is washed with 1N HCl (30 mL×3) and brine(30 mL), dried over Na$_2$SO$_4$, and the solvent is removed under reduced pressure to obtain the crude product. Products can be further purified by silica gel column chromatography or the like.

Condition E is a procedure for the large-scale oxidation of an olefin. In Condition E, the olefin (9 g) is dissolved in DMF (250 mL), and OsO$_4$ (0.2 mL, 2.5% in tBuOH, 0.0002 eq) is added and the mixture stirred for five minutes. OXONE (123 g) is then added slowly via a solid addition funnel over 2 hours. The reaction is stirred at room temperature for 6 hours followed by addition of Na$_2$SO$_3$ (54 g) and then stirred for an additional hour. The reaction is diluted with Et$_2$O (750 mL) and stirred for 10 min. The solid is filtered off and washed with Et$_2$O (75 mL×3). The organic extract is washed with 1N HCl (200 mL×3) and brine (200 mL) and dried over Na$_2$SO$_4$. The solvent is removed under reduced pressure to obtain the product at 11.60 g and 95% yield. Products can be further purified by silica gel column chromatography or the like.

Condition F is a general procedure for the preparation of an aldehyde from an olefin using Condition F. In Condition F, the olefin (100 mg, 1 eq) is dissolved in freshly distilled CH$_2$Cl$_2$ (5 mL, 0.1 M), and OsO$_4$ (0.076 mL, 2.5% in tBuOH, 0.01 eq) is added and the mixture stirred for 5 min. Tetrabutylammoniumperoxysulfate (450 mg, 90% pure, 2 eq) is added in one portion. The reaction is stirred at room temperature for 3 hours or until the solution becomes colorless. This usually marks the completion of the reaction which can be verified by TLC. Na$_2$SO$_3$ (600 mg, 6 eq w/w) is added, to reduce the remaining Os(VIII), and the mixture stirred for an additional hour or until solution becomes dark brown/black. The solvent is removed under reduced pressure to obtain the crude product. Products can be further purified by silica gel column chromatography or the like.

Condition G is a general procedure for the preparation of an aldehyde from an olefin. In Condition G, the olefin (100 mg, 1 eq) is dissolved in freshly distilled $CH_2Cl_2$ (5 mL, 0.1M), and $OsO_4$ (0.38 mL, 2.5% in tBuOH, 0.05 eq) is added and the mixture stirred for 5 min. OXONE (676 mg, 2 eq) is added in one portion. The reaction is stirred at room temperature and monitored by GC for 36 hours. $Na_2SO_3$ (600 mg, 6 eq w/w) is added to reduce the remaining Os(VIII) and the mixture stirred for an additional hour or until solution becomes dark brown/black. The solvent is removed under reduced pressure to obtain the crude product. Products can be further purified by silica gel column chromatography or the like.

Condition H is a procedure for the preparation of an ester from an olefin. In Condition H, the olefin (100 mg) is dissolved in MeOH (5 mL), and $OsO_4$ (0.076 mL, 2.5% in tBuOH) is added and the mixture stirred for 5 min. OXONE (1.35 g) is added in one portion. The reaction is stirred at room temperature for 18 hours or until the solution becomes colorless. This usually marks the completion of the reaction which can be verified by TLC or GC. $Na_2SO_3$ (540 mg) is added to reduce the remaining Os(VIII) and the mixture stirred for an additional hour or until solution becomes dark brown/black. The solvent is removed under reduced pressure and EtOAc is then added to extract the products and 1N HCl is used to dissolve the salts. The organic extract is washed with 1N HCl (30 mL×3) and brine (30 mL), dried over $Na_2SO4$, and the solvent is removed under reduced pressure to obtain the crude product. Products can be further purified by silica gel column chromatography or the like.

Condition I is a general procedure for the oxidation of aldehydes to esters. In Condition I, the aldehyde (1 eq) is dissolved in MeOH (0.2 M), and OXONE (1 eq) is added and the mixture stirred at room temperature for 18 hours. The reaction is monitored by TLC or GC analysis. EtOAc is added to extract the products and 1N HCl is used to dissolve the salts. The organic extract is washed with 1N HCl (3×) and brine, dried over $Na_2SO_4$, and the solvent is removed under reduced pressure to obtain the crude product. Products can be further purified by silica gel column chromatography or the like.

Condition J is a general procedure for the oxidation of aldehydes to carboxylic acids. In Condition J, the aldehyde (1 eq) is dissolved in DMF (0.2 M), and OXONE (1 eq) is added and the mixture stirred at room temperature for 3 hours. The reaction is monitored by TLC or GC analysis. EtOAc is added to extract the products and 1N HCl is used to dissolve the salts. The organic extract is washed with 1N HCl (3×) and brine, dried over $Na_2SO_4$, and the solvent is removed under reduced pressure to obtain the crude product. Products can be further purified by silica gel column chromatography or the like.

In summary, the key features that makes the process of the present invention more advantageous than the earlier processes is that the diol intermediate is no longer formed as with the prior art metal-assisted cleavage processes. Also, the process of the present invention does not require an elaborate setup such as is required for the production of ozone and the intermediates formed do not pose the risk of explosion. Finally, the process of the present invention is versatile in terms of both oxidation state obtained and functionalities of the substrate that are tolerated.

Because $OsO_4$ has been reported to be toxic, in particular the osmium metal, to reduce the risk of toxic exposure to the osmium metal, the process of the present invention preferably uses small quantities of the catalyst and preferably uses commercially available stock solutions of the of catalyst. For example, potassium osmate ($K_2OSO_4*2H_2O$) or $OsCl_3$, which represent reduced forms of $OSO_4$, are reportedly less toxic to handle. Potassium osmate is used commercially on large scale in the production of chiral diols. $K_2OsO_4*2H_2O$ had a catalytic effect that was similar to that of $OsO_4$ in the process of the present invention. Another means for reducing toxic exposure to the osmium metal is containing the osmium catalyst within a polymer support such as PEM or poly(4-vinylpyridine). Containing the osmium catalyst within a polymer support not only facilitates the ease of workup following the reaction but also reduces the risk of contact with the catalyst.

The markets that will benefit from the process of the present invention include the pharmaceutical, paper, and petroleum industries. For example, recent patents assigned to several pharmaceutical companies disclose ozonolysis reactions for producing drugs (e.g., U.S. Pat. No. 5,438,118 to Callahan et al. and U.S. Pat. No. 5,302,589 to Frye et al.). The paper industry has recently phased out bleach as an oxidant as a means for decolorizing or bleaching recycled paper. They have relied on ozonolysis for the bleaching. The process of the present invention can be used as a means for decolorizing recycled paper that is safe and efficient. As stated above, the petroleum industry is the primary source of many commercially available organic compounds (e.g., Jacobsen et al., J. Am. Oil Chem. Soc. 71: 653_65 5 (1994); Mhaskar et al., J. Am. Oil Chem. Soc. 71: 543_544 (1994); Kula et al., J. Am. Oil Chem. Soc. 71: 545_546 (1994); Rebrovic, J. Am. Oil Chem. Soc. 69: 159_165 (1992); Bunce et al., Org. Prep. Proced. Int. 19: 67_71 (1987); Karim et al., Org. Prep. Proced. Int. 22: 648_650 (1990)). The above industries are interested in preparing organic compounds that have a large commercial demand in high purity and in high yields. The process of the present invention provides an improved process that satisfies the needs of the above industries. A further advantage of the present invention is that commercially available and inexpensive starting materials are used for the catalyst, oxidant and solvent. The process of the present invention is also attractive because the process does not require special construction of facilities; the reactions can easily be performed in any existing chemical reactor.

The following examples are intended to promote a further understanding of the present invention.

EXAMPLE 1

This example demonstrates the oxidation of simple alkyl and aromatic olefins such as stilbene or cyclohexene to a carboxylic acid in dimethyl formamide (DMF) containing $OsO_4$ and OXONE.

All commercially available starting material were used without purification. Except for cyclohexene (6) (Fisher) and methyl oleate (11) (Nu-Chek-Prep), all commercially available starting materials were obtained from Aldrich. $^1$H, $^{13}$C, 2D-COSY, and DEPT spectra were recorded on 300 MHz NMR spectrometer (Varian Nova) in $CDCl_3$. IR spectra were recorded on Nicolet IR/42 spectrometer using NaCl cells. Column chromatography was performed using SILI-CYCLE (40–60 µm) silica gel. Analytical TLC was done using pre-coated silica gel 60 F254 plates. GC analysis was performed using HP (6890 series) GC system (Column type-AltechSE-54, 30×320 µm×0.25 µm).

All reactions were performed with the olefin (1 eq.), OXONE (4 eq.), and $OsO_4$ (0.01 eq.) in DMF (0.2 M) for three hours at room temperature. In a typical reaction, 1 eq. of the olefin was dissolved in 0.2 M DMF in a round bottom flask. Next, 0.01 eq. of $OsO_4$ (2.5% solution in t-butanol)

was added to the flask and the solution stirred for about 5 minutes. Then, 4 eq. of OXONE was added in one portion and the solution was incubated at room temperature with constant stirring for about 3 hours or until the solution became colorless. Next, to ease removal of the $OsO_4$ from the solution, $Na_2SO_3$ was added to the solution in an amount that was 6 times by weight of the original (SM) olefin, which was an amount sufficient to reduce the $OsO_4$, and the solution was stirred for about one hour or until the solution turned a dark brown or black. Work-up was by dissolving the salts in 1N HCl and then extracting the solution with EtOAc. The extract was washed three times with 1N HCl and once with a brine solution. The washed extract was dried over $Na_2SO_4$, filtered, and the solvent removed to produce the organic product. In some cases, a silica gel column was used to purify the product. The organic product was dried under a vacuum prior to analysis by nuclear magnetic resonance (NMR).

Figure 7A:
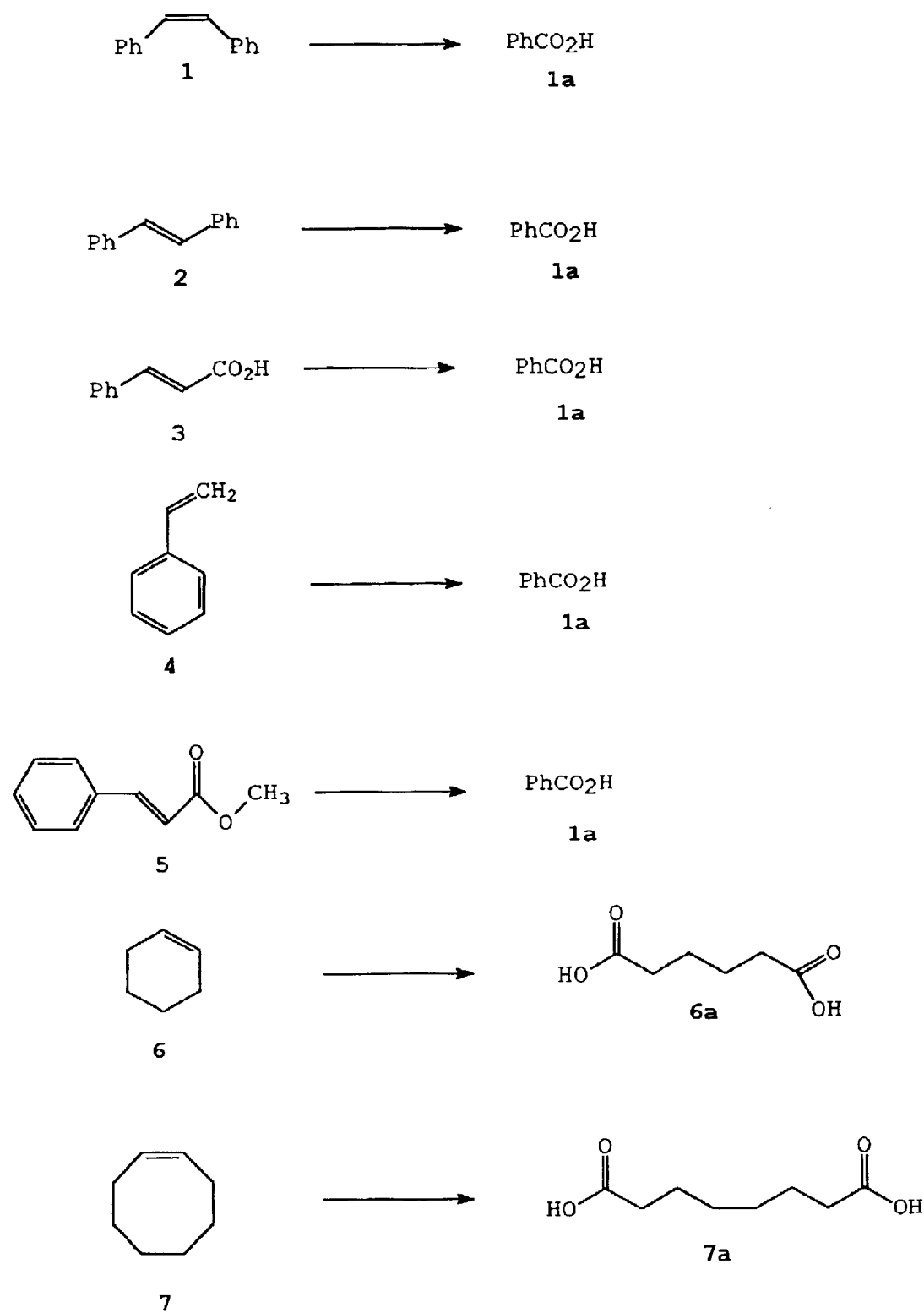
FIG. 7a shows the chemical structures for the substrates cis-stilbene (1), trans-stilbene (2), trans-cinnamic acid (3), styrene (4), methyl cinnamate (5), cyclohexene (6), and cyclooctene (7) and oxidative cleavage products benzoic acid (1a), adipic acid (6a), and suberic acid (7a) which are identified in Table 1.
Figure 7B:
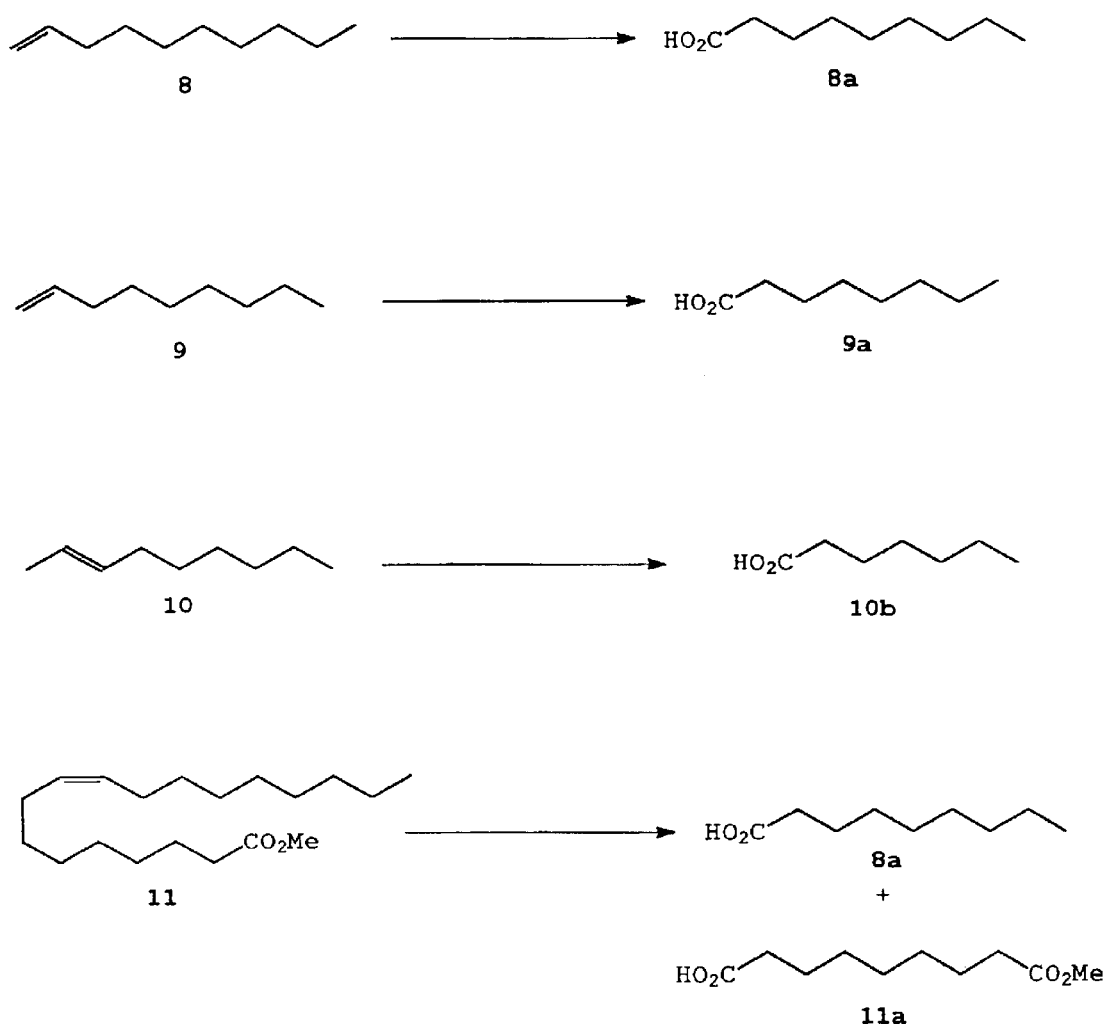
FIG. 7b shows the chemical structures for the substrates 1-decene (8), 1-nonene (9), 2-trans-nonene (10), and methyl oleate (11) and oxidative cleavage products nonanoic acid (8a), octanoic acid (9a), heptanoic acid (10a), and nonanedioic acid monomethyl ester (11a) which are identified in Table 1.

The results of the oxidation of the simple alkyl aromatic olefins to carboxylic acids using the process of the present invention are shown in Table 1 and FIGS. 7a and 7b. The process of the present invention oxidized both cis- and trans-stilbene (1 and 2) to two equivalents of benzoic acid (1a) in 95% yield. Trans-cinnamic acid (3), styrene (4), and methyl cinnamate (5) were also easily oxidized by the process of the present invention to 1a in 97%, 94% and 96% yields, respectively. Cyclohexene (6) was oxidized by the process of the present invention to the desired adipic acid (6a) but in a reduced yield, 50%, presumably due to its water solubility. However, cyclooctene (7) was easily oxidized by the process of the present invention to suberic acid (7a) with a yield of 82%. Additionally, simple alkyl olefins such as 1-decene (8), 1-nonene (9), and trans-2-nonene (10), all provided the appropriate alkyl carboxylic acids 8a, 9a, and 10a, respectively, in 93%, 90%, and 93% yields, respectively. Similarly, methyl oleate (11) provided a clean conversion to nonanoic acid (8a) and nonanedoic acid monomethyl ester (11a).

TABLE 1[a]

| Substrate | Product | Yield(%)[b] |
|---|---|---|
| cis-stilbene (1) | benzoic acid (1a) | 95 |
| trans-stilbene (2) | 1a | 95 |
| trans-cinnamic acid (3) | 1a | 97 |
| styrene (4) | 1a | 94 |
| methyl cinnamate (5) | 1a | 96 |
| cyclohexane (6) | adipic acid (6a) | 50(94)[c] |
| cyclooctene (7) | suberic acid (7a) | 82(92)[c] |
| 1-decene (8) | nonanoic acid (8a) | 93 |
| 1-nonene (9) | octanoic acid (9a) | 90 |
| 2-trans-nonene (10) | heptanoic acid (10a) | 93 |
| methyl oleate (11) | 8a + 11a | 80(93)[c] |

[a]All reaction were performed with 1 eq. olefin, 4 eq. OXONE, and 0.01 eq. $OsO_4$ in DMF for 3 hours at room temperature.
[b]Isolated yields
[c]GC yield The spectral data for the benzoic acid (1a), adipic acid (6a), suberic acid (7a), nonanoic acid (8a), octanoic acid (9a), and heptanoic acid (10a) matched the spectral data reported by Aldrich (Sigma-Aldrich, St. Louis, Mo.).

A number of mono-substituted, 1,1-disubstituted, 1,2-disubstituted, tri-substituted, and tetra-substituted olefins containing a variety of functional groups were also subjected to the oxidative cleavage as shown in Example 4. In most cases, a yield of 80% or greater of the desired ketone or carboxylic acid was obtained.

EXAMPLE 2

To further highlight the utility of the oxidative cleavage of the present invention, reactions using compounds 2 to 7 have been successfully scaled up to 50 mmol (9 g) and the amount of osmium that used in the reactions has been greatly reduced from 5 mol % to 0.02 mol % (about 5,000 turnovers of the osmium). The isolated yields from these reactions remained high at 95% crude or 88% after crystallization from chloroform.

EXAMPLE 3

It was discovered that the reaction of the present invention can proceed in solvents other than dimethyl formamide and that the type of solvent determined the product that was produced.

For example, as shown in Scheme 7 of FIG. 8, when trans-stilbene was the substrate and the reaction with $OsO_4$ and OXONE was performed using dichloromethane (DCM) as the solvent, the reaction was stopped at the aldehyde step enabling the aldehyde intermediate to be recovered. As shown in Scheme 8 of FIG. 8, when trans-stilbene was the substrate and the reaction with $OsO_4$ and OXONE was performed in methanol, the aldehyde intermediate was oxidized to a methyl ester. Both reactions had been performed with 1 eq. of trans-stilbene, 0.05 eq. of $OsO_4$, and 4 eq. of OXONE in the appropriate solvent. It is expected that other solvents will also determine the product that is produced in the reaction.

Thus, the results show that a selective oxidative cleavage of olefins, which results in their oxidation to ketones or carboxylic acids, is both simple and effective using $OsO_4$ and OXONE in DMF.

EXAMPLE 4

This example shows that the process of the present invention is able to convert a number of mono-substituted, 1,1-di-substituted, tri-substituted, and tetra-substituted olefins to desirable ketone or acid products in dimethyl formamide (DMF) containing $OsO_4$ and OXONE. The structures for the olefins that were used are shown in FIGS. 9a, 9b, 9c, and 9d.

All commercially available starting material were used without purification. Except for nootkatoone (22) (Lancaster), all commercially available starting materials were obtained from Aldrich. Compounds 20 and 23 were prepared as reported previously (McMurry et al., J. Org. Chem. 43: 3255–3266 (1978) and Macaulay, J. Org. Chem. 45: 734–735 (1980), respectively). $^1H$, $^{13}C$, 2D-COSY, and DEPT spectra were recorded on 300 MHz NMR spectrometer (Varian Nova) in $CDCl_3$ except 21b, which was recorded on a 500 MHz NMR spectrometer (Varian VXR) in $CDCl_3$. IR spectra were recorded on Nicolet IR/42 spectrometer using NaCl cells. Column chromatography was performed using SILICYCLE (40–60 $\mu$m) silica gel. Analytical TLC was done using pre-coated silica gel 60 F254 plates. GC analysis was performed using HP (6890 series) GC system (Column type-AltechSE-54, 30×320 $\mu$m×0.25 $\mu$m).

In general, the reactions were performed under Condition A or Condition B. Under Condition A, the olefin (1 eq.) was dissolved in DMF (0.2 M), and $OsO_4$ (0.01 eq., 2.5% in tBuOH) was added and stirred for 5 min. OXONE (4 eq.) was added in one portion and the reaction was stirred at Room temperature for 3 hours or until the solution becomes colorless. This usually marks the completion of the reaction which was verified by TLC or GC. Na$_2$SO$_3$ (6 eq. w/w) was added, to reduce the remaining Os(VIII), and stirred for an additional hour or until solution became dark brown/black. EtOAc was added to extract the products and 1N HCl was used to dissolve the salts. The organic extract was washed with 1N HCl (3×) and brine, dried over Na$_2$SO$_4$, and the solvent was removed under reduced pressure to obtain the crude product. Products were purified by silica gel column chromatography.

Under Condition B, the olefin (1 eq.) was dissolved in DMF (0.2 M), and OsO$_4$ (0.01 eq., 2.5% in tBuOH) was added and stirred for 5 min. A solid mixture of OXONE (4 eq.) and NaHCO$_3$ (4 eq.) was then added in one portion and the reaction was stirred at room temperature for 3 hours or until solution becomes colorless. This usually marks the completion of the reaction which was verified by TLC or GC. Na$_2$SO$_3$ (6 eq. w/w) was added, to reduce the remaining Os(VIII), and stirred for an additional hour or until solution became dark brown/black. EtOAc was added to extract the products and 1N HCl was used to dissolve the salts. The organic extract was washed with 1N HCl (3×) and brine, dried over Na$_2$SO$_4$, and the solvent was removed under reduced pressure to obtain the crude product. Products were purified by silica gel column chromatography. For the reaction with isopulegol (13), only 2 eq. of the OXONE was used. The particular reactions were as follows.

To prepare 9-decenyl acetate (12), to a solution of 9-decene-1-ol (500 mg, 3.2 mmol) in pyridine (10 mL) was added acetic anhydride (0.91 mL, 9.6 mmol). The mixture was stirred and heated for 3 hours at 60° C. The reaction was then extracted with EtOAc (25 mL) and washed with 1 N HCl (25 mL×5) and brine (25 mL). The organic layer was dried over Na$_2$SO$_4$ and concentrated under reduced pressure to provide a crude, slightly yellow oil. Column chromatography (5% EtOAc/hexanes) provided the desired acetate (630 mg, 99% yield).

To prepare (1R,2S,5R)-(2-isoprenyl-5-methyl-cyclohexyl)benzyl ether (14), sodium hydride (68 mg, 60% dispersion in mineral oil, 1.7 mmol) was suspended in dry THF (9 mL). The reaction mixture was cooled to 0° C. and isopulegol (200 mg, 1.3 mmol) dissolved in dry THF (1 mL) was added and the reaction stirred for 30 minutes. Benzyl bromide (289 mg, 1.7 mmol) and KI (63 mg, 1.7 mmol) were added sequentially at 0° C. The reaction mixture was allowed to warm to room temperature and stirred for an additional three hours after which the reaction mixture was quenched with water and saturated NH$_4$Cl and then extracted into EtOAc (20 mL×2). The combined organics were washed with water (40 mL) and brine (40 mL), dried over Na$_2$SO$_4$ and the solvent removed under reduced pressure to obtain a slightly colored oil. Column chromatography (10% EtOAc/hexanes) provided the desired benzyl ether 14 (278 mg, 88%).

To highlight the fact that 1,2-diols do not oxidize under the reaction conditions herein to yield product, and thus are not intermediates during the cleavage, two test reactions were performed with both styrene glycol and methyl 9,20-dihydroxyoctadecanoate. In both cases, their corresponding olefinic counterparts, i.e., styrene and methyl 9,10-octadecenoate were also subjected to the reaction simultaneously using OXONE (2 eq.), OsO$_4$ (0.01 eq.) at 3 hours at room temperature. The reactions were monitored by 1H-NMR, TLC, and GC. The results clearly showed that the olefins were cleanly oxidized to the corresponding carboxylic acids, however, the diols in both cases remained untouched and were recovered in near quantitative yields.

OsO$_4$ does not cleave 1,2-diols independently. From the latter experiment and the prior art, it is clear the OXONE also does not cleave or oxidize alcohols or 1,2-diols without other cofactors present (Bressan et al., J. Molec. Catal. 79: 85–93 (1993); Bolm et al., Org. Lett. 2: 1173–1175 (2000); Hajipour et al., Chem. Lett. 460–461 (2000); Hirano et al., Bull. Chem. Soc. Jpn. 64: 1046–1047 (1991)). Thus it is reasonable to assume that the oxidative cleavage of the present invention proceeds without the formation of an intermediate 1,2-diol and in fact, the osmate ester is activated for the direct cleavage of the C—C bond.

In most of the reactions, a yield of 80% or greater was obtained. The results are shown in Table 2.

TABLE 2[a]

| Substrate | Product | Yield (%) |
|---|---|---|
| 9-decenyl acetate (12) | 12a | 93 |
| (−)-isopulegol (13) | 13a, 13b | 44, 34 |
| benzyl-protected isopulegol (14) | 14a | 80 |
| 4,4'-dimethyl stilbene (15) | 15a | 91 |
| 4,4-dinitro stilbene (16) | 16a | 95 |
| 2-cyclohexeneone (17) | 17a | 92[b] |
| α-methylcinammic acid (18) | 1a | 82(90)[b,c] |
| methylcyclohexene (19) | 19a | 80(85)[b,c] |
| tetra-substituted olefin (20) | 20a | 85[c] |
| (+)-pulegone (21) | 21a, 21b | 67[c] |
| nootkatone (22) | 22a | 60[d] |
| alkyne (23) | recovered 23 | — |
| careen (24) | 24a + (24b, 24c) | 50 24ab + (30 combined 24b, 24c) |

[a]All reactions were preformed with 1 eq. olefin, 4 eq. OXONE, and 0.01 eq. OsO4 in 0.2 M DMF for 3 hours at room temperature.
[b]GC yield.
[c]4 eq. NaCO$_3$.
[d]Only 2 eq. OXONE was used.

As shown in Table 2, 9-decene acetate (12) reacted smoothly to provide the carboxylic acid 9-acetoxy nonanoic acid (12a) in 93% yield. The alcohol functionality within the molecule appeared to be tolerated well in the case of isopulegol (13) which provided a combined yield of 78% of which (1R,2R,5R)-2-acetyl-5-methyl cyclohexanol (13a) was 44% and 34% was (1R,2R,5R)-2-acetyl-5-methyl cyclohexanol formate (13b). However, in contrast, the benzyl-protected version of this alcohol (14) provided 80% of the desired ketone, (1R,2R,5R)-(2-acetyl-5-methyl cyclohexyl)benzyl ether (14a). 13b and 14a are novel products. Substituted stilbenes 15 and 16 were cleanly converted into the corresponding acid products 15a and 16a, respectively, without difficulty in 91% and 95% yields, respectively.

Interestingly, α-methyl cinnamic acid (18) and 1-methylcyclohexene (19) (examples of tri-substituted olefins) did not deliver the desired product in high yields under standard conditions. Seemingly, the hydrolysis of the osmate intermediate leads to the formation of the observed diol side product, presumably as a result of the acidity of OXONE. However, the addition of solid NaHCO$_3$ to the reaction substantially improved the yields of the oxidatively cleaved products benzoic acid (1a) and 6-oxyheptanoic acid (19a), respectively. Cleavage of the tetra-substituted olefin 20 in the presence of NaHCO$_3$ was also successful in yielding acetophenone (20a).

α,β-Unsaturated systems pose an interesting case since their cleavage would yield an α-dicarbonyl functionality. Oxidation of 2-cyclohexeneone (17) provided pentanedioic acid (17a), most likely via the α-carbonyl intermediate which decarboxylates under oxidative conditions. Baeyer-Villiger-like oxidative cleavage of α-carbonyls have been reported previously with peroxy compounds and is likely the operative route in the latter oxidation. 1,2-Cyclohexanedione subjected to the same reaction conditions (without $OsO_4$) was also oxidized to adipic acid (80%), thus demonstrating the lability of the α-dicarbonyl functionality. In a similar fashion, (+)-pulegone (21) yielded the dicarboxylic acid 21a via the intermediacy of an α-diketone and 3R,7-dimethyl-6-oxo-octanoic acid (21b).

Treatment of nootkatone (22) containing dissimilar olefins under standard conditions furnished the ketone (4S,4aR,6R)-6-acetyl-4,4a-dimethyl-4,4a,5,6,7,8-hexahydro-3H-naphthalen-2-one (22a) showing that selectivity in oxidation is also obtainable. Lastly, the alkyne 15-hexadecynyl acetate (23) was subjected to the above cleavage conditions, however, it proved immune to oxidation and only the starting material was recovered. The result indicates that the oxidative cleavage reactions of the present invention are selective for oxidative cleavage of alkenes and not alkynes.

The oxidation of the tri-substituted olefin careen (24) produced lower yields of the ketoacid (24a) (50%). The side products of the careen reaction were determined to be diol formation (24b) and a mono formulated diol (24c), which together provided a 30% yield. These two products were never isolated in the exact same percentage in different runs, but the total percentage of the two together was always about 30%.

The spectral data for 12 was $^1H$ NMR ($CDCl_3$, 300 MHz): δ5.74–5.83 (m, 1H), 4.89–4.99 (m, 2H), 4.03 (t, 2H, J=6.9 Hz), 2.02 (s, 3H), 2.01–2.07 (m, 2H), 1.56–1.62 (m, 2H), 1.27–1.38 (m, 10H); $^{13}C$ NMR ($CDCl_3$, 75 MHz): δ171.2, 139.0, 114.1, 64.6, 33.7, 29.3, 29.1, 28.9, 28.7, 28.5, 25.8, 20.9; IR (neat, NaCl, $cm^{-1}$) 3077, 2927, 2856, 1741, 1641, 1242; LRMS (70 eV, ET) m/z 138$[M-OAc]^+$.

The spectral data for 12a was $^1H$ NMR ($CDCl_3$, 300 MHz): δ4.02 (t, 2H, J=6.9 Hz), 2.32 (t, 2H J=7.4 Hz), 2.02 (s, 3H), 1.56–1.61 (m, 4H), 1.29 (bs, 8H); $^{13}C$ NMR ($CDCl_3$, 75 MHz): δ179.6, 171.4, 64.5, 33.9, 29.0, 28.9, 28.8, 28.4, 25.7, 24.5, 20.9; IR (neat, NaCl, $cm^{-1}$) 3455, 2931, 2856, 1739, 1737, 1242; LRMS (70 eV, EI) m/z 199 $[M-H_2O]^+$, 157$[M-OAc]^+$.

The spectral data for 13a was 1H NMR ($CDCl_3$, 300 MHz): 5 3.80 (ddd, 1H, J=4.4, 9.6, 11.1 Hz), 2.27 (ddd, 1H, J-3.6, 9.6, 12.9 Hz), 2.17 (s, 3H), 1.91–2.00 (m, 2H), 1.68–1.74 (m, 1H), 1.38–1.52 (m, 1H), 1.22–1.27 (m, 1H), 0.91–1.03 (m, 1H), 0.92 (d, 3H, J=6.3 Hz); IR (neat, NaCl, $cm^{-1}$) 3417, 2952, 2927, 2869, 1705; LRMS (70 eV, ET) m/z 156 $M^+$, 138$[M-H_2O]^+$, 95$[M-H_2O—C(O)Me]^+$.

The spectral data for 13b was $^1H$ NMR ($CDCl_3$, 300 MHz): δ7.95 (s, 1H) 5.06 (ddd, 1H, J=4.4, 9.6, 11.2 Hz), 2.59 (ddd, 1H, J=6.9, 8.9, 14.5 Hz), 2.15 (s, 3H), 2.11–2.13 (m, 1H), 1.93 (qd, 1H, J=3.9, 6.9 Hz), 1.68–1.77 (m, 1H), 1.50–1.62 (m, 1H), 1.27–1.41 (m, 1H), 0.87–1.06 (m, 4H); $^{13}C$ NMR ($CDCl_3$, 75 MHz): δ209.4, 160.3, 73.1, 55.2, 39.3, 33.3, 30.0, 29.3, 27.8, 21.7; IR (neat, NaCl, $cm^{-1}$) 2952, 2929, 2869, 1728, 1178; LRMS (70 eV, EI) m/z 185 $[M+H]^+$, 149 $[M-HCO_2H]^+$; MRMS $[M+H]^+$ calculated for $c_{10}H_{16}O_3$: 184.1099 m/z, observed 184.1095 m/z.

The spectral data for 14 was $^1H$ NMR ($CDCl_3$, 300 MHz): δ7.25–7.43 (m, 5H), 4.83 (s, 2H), 4.61 (t, 1H, J=11.5 Hz), 4.52 (d, 1H, J=11.8 Hz), 3.31 (dt, 1H, J=4.1, 10.7 Hz), 2.11 (m, 2H), 1.71 (s, 3H), 1.64 (m, 2H), 1.28–1.45 (m, 2H), 0.95–1.06 (m, 5H); $^{13}C$ NMR ($CDCl_3$, 75 MHz): δ147.8, 139.1, 128.3, 128.1, 127.7, 127.6, 127.2, 110.9, 79.1, 70.3, 51.7, 40.2, 34.3, 31.5, 31.0, 22.3, 20.0; IR (neat, NaCl, $cm^{-1}$) 2923, 2867, 1106; LRMS (70 eV, EI) m/z 243 $[M-H]^+$, 138 $[M-OBn]^+$.

The spectral data for 14a was $^1H$ NMR ($CDCl_3$, 300 MHz) δ7.21–7.32 (m, 5H), 4.56 (d, 1H, J=11.3 Hz), 4.37 (d, 1H, J=11.3 Hz), 3.6 (dt, 1H, J=6, 10.4 Hz), 2.53 (ddd, 1H, J=3.8, 10.1, 12.6 Hz), 2.16 (s, 3H), 2.12–2.19 (m, 1H), 1.75 (qd, 1H, J=3.6, 10.2 Hz), 1.64–1.70 (m, 1H), 1.25–1.52 (m, 2H), 0.93 (d, 2H, J=3.3 Hz); $^{13}C$ NMR ($CDCl_3$, 75 mHz): δ212.3, 138.5, 128.2, 127.6, 127.4, 79.1, 70.9, 56.6, 39.4, 33.5, 30.9, 27.7, 22.1; IR (neat, NaCl, $cm^{-1}$) 2950, 2927, 2867, 1739, 1712; LRMS (70 eV, EI) m/z 228 $[M-H_2O]^+$, 140$[M-OBn]^+$; HRMS $[M+H]^+$ calculated for $C_{16}H_{22}O_2$: 246.1620 m/z, observed 246.1631 m/z.

The spectral data for 19a was $^1H$ NMR ($CDCl_3$, 300 MHz): δ2.41–2.45 (m, 2H), 2.31–2.36 (m, 2H), 2.11 (s, 3H), 1.56–1.62 (m, 4H); $^{13}C$ NMR ($CDCl_3$, 75 mHz): δ208.8, 179.1, 43.2, 33.7, 29.9, 24.0, 22.9; IR (neat, NaCl, $cm^{-1}$) 3455, 2939, 1714; LRMS (70 eV, EI) m/z 144 $M^+$, 126 $[M-H_2O]^+$.

The spectral data for 21a was $^1H$ NMR ($CDCl_3$, 300 MHz) δ2.57 (p, 1H, J=7.0 Hz), 2.46 (dt, 1H, J=6.2, 9.1 Hz), 2.32 (dd, 1H, J=6.0, 15.3 Hz), 2.16 (dd, 1H, J=6.9, 15.3 Hz), 1.93 (sept, 1H, J=6.6 Hz), 1.63 (m, 1H), 1.48 (m, 1H), 1.07 (d, 6H, J=6.8 Hz), 0.95 (d, 3H, J=6.7 Hz); $^{13}C$ NMR ($CDCl_3$, 125 mHz): δ214.5, 178.3, 41.2, 40.9, 37.8, 30.2, 29.8, 19.5, 18.3; IR (neat, NaCl, $cm^{-1}$) 3164, 2964, 2933, 1706, 1384, 1465; LRMS (70 eV, EI) m/z 186 $M^+$, 168$[M-H_2O]^+$, 143 $[M-C_3H_7]^+$.

The spectral data for 22a was $^1H$ NMR ($CDCl_3$, 300 MHz): δ5.72 (s, 1H), 2.71 (m, 1H), 2.33–248 (m, 2H), 2.20–2.25 (m, 2H), 2.1 (s, 2H), 1.94–2.06 (m, 4H), 1.40 (m, 1H), 1.21 (t, 1H), J=12.5 Hz, 1.06 (s, 3H), 0.93 (dd, 3H, J=6.6, 1.9 Hz); $^{13}C$ NMR ($CDCl_3$, 75 mHz): δ210.4, 199.2, 168.5, 125.1, 46.6, 41.9, 40.1, 39.8, 38.8, 31.9, 28.4, 28.1, 16.6, 14.8; IR (neat, NaCl, $cm^{-1}$) 2966, 2939, 2883, 1708, 1668, 1617; LRMS (70 eV, EI) m/z 220 $M^+$, 177$[M-COMe]^+$.

The spectral data for the remainder of the compounds matched those reported by Aldrich and comparison to authentic samples. The above results show that selective oxidative cleavage of substituted olefins is both simple and effective using $OsO_4$ and OXONE in DMF.

EXAMPLE 5

This example shows the oxidation of benzaldehyde in interactive solvents containing OXONE. The benzaldehyde can also be an intermediate produced by reacting styrene with 0.05 eq. $OsO_4$ and 1 eq. OXONE in the interactive solvent for about 24 hours at room temperature. The benzaldehyde that is produced is further oxidized by the OXONE to benzyl ester in the interactive solvent as shown in this example.

FIG. 3 shows the product that was produced when benzaldehyde was reacted with 1 eq. OXONE in the interactive solvent methanol, ethanol, n-propanol, isopropanol, or tert-butanol for about 24 hours at room temperature. When the solvent was methanol, the product that was produced was a benzyl methyl ester in about 96% yield. When the solvent was ethanol, the product that was produced was a benzyl ethyl ester in about 90% yield. When the solvent was n-propanol, the product that was produced was a benzyl propyl ester in about 94% yield. When the solvent was isopropanol, the product that was produced was a benzyl propyl ester in about 95% yield. When the solvent was tert-butanol, the product that was produced was benzoic acid in about 98% yield.

EXAMPLE 6

This example shows the oxidation of several aldehydes in methanol containing OXONE. The aldehydes can also be an intermediate produced by reacting the parent olefin with 0.05 eq. $OsO_4$ and 1 eq. OXONE in the methanol for about six hours at room temperature. The aldehydes that are produced are further oxidized by the OXONE to the methyl ester in the methanol as shown in this example.

FIG. 4 shows the methyl esters that were formed from the various aldehydes when the aldehydes were incubated in methanol containing 1 eq. OXONE for six hours at room temperature.

EXAMPLE 7

This example shows the effect of the groups on aromatic aldehydes on its oxidation in dimethyl formamide (DMF) containing OXONE. The aromatic aldehyde can also be an intermediate produced by reacting an olefin with 0.01 eq. $OsO_4$ and 4 eq. OXONE in DMF for about three to 24 hours at room temperature. The aromatic aldehydes that are produced are further oxidized by the OXONE to the carboxylic acid as shown in this example.

As shown in FIG. 5, when the X group in the aromatic aldehyde was the electron withdrawing group $NO_2$, CN, Cl, $CO_2Me$, H, or Me, the aldehyde was oxidized by 1 eq. OXONE to a carboxylic acid with a yield of 95%, 85%, 97%, 95%, 97%, or 97%, respectively. However, when the X group in the aromatic aldehyde was the electron donating group OH or MeO, the aldehyde was oxidized by 1 eq. OXONE to a mixture of the carboxylic acid (19% or 31%, respectively) and the formate ester (62% or 58%, respectively).

EXAMPLE 8

This example shows the oxidation of various aldehydes in dimethyl formamide (DMF) containing OXONE. The aldehydes shown can also be an intermediate produced by reacting the corresponding parent olefin with 0.05 eq. $OsO_4$ and 1 eq. OXONE in DMF for about three hours at room temperature. The aldehydes that are produced are further oxidized by the OXONE to the products as shown in this example.

FIG. 6 shows the products that were formed by the oxidation of the various aldehydes by 1 eq. OXONE in DMF for three hours at room temperature.

EXAMPLE 9

This example shows the oxidation of cis-stilbene using Condition A.

cis-Stilbene (90 mg) was dissolved in DMF (5 mL), and $OsO_4$ (0.06 mL, 2.5% in tBuOH) was added and stirred for 5 min. OXONE (1.23 g) was added in one portion and the reaction had a final volume (7 mL). The reaction was stirred at room temperature for 3 hours or until the solution becomes colorless. This usually marks the completion of the reaction which was verified by TLC or GC. $Na_2SO_3$ (540 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain the crude product. Benzoic acid was obtained in 95% yield without the need for further purification.

EXAMPLE 10

This example shows the oxidation of trans-stilbene using Condition A.

trans-Stilbene (90 mg) was dissolved in DMF (5 mL), and $OsO_4$ (0.06 mL, 2.5% in tBuOH) was added and stirred for 5 min. OXONE (1.23 g) was added in one portion and the reaction had a final volume (7 mL). The reaction was stirred at room temperature for 3 hours or until the solution becomes colorless. This usually marks the completion of the reaction which was verified by TLC or GC. $Na_2SO_3$ (540 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain the crude product. Benzoic acid was obtained in 95% yield without the need for further purification.

EXAMPLE 11

This example shows the oxidation of trans-cinnamic acid using Condition A.

trans-Cinnamic Acid (74 mg) was dissolved in DMF (5 mL), and $OsO_4$ (0.06 mL, 2.5% in tBuOH) was added and stirred for 5 min. OXONE (1.23 g) was added in one portion and the reaction had a final volume (7 mL). The reaction was stirred at room temperature for 3 hours or until the solution becomes colorless. This usually marks the completion of the reaction which was verified by TLC or GC. $Na_2SO_3$ (450 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain the crude product. Benzoic acid was obtained in 97% yield without the need for further purification.

EXAMPLE 12

This example shows the Oxidation of styrene using Condition A.

Styrene (100 mg) was dissolved in DMF (10 mL), and $OsO_4$ (0.12 mL, 2.5% in tBuOH) was added and stirred for 5 min. OXONE (2.36 g) was added in one portion and the reaction had a final volume (13 mL). The reaction was stirred at room temperature for 3 hours or until the solution becomes colorless. This usually marks the completion of the reaction which was verified by TLC or GC. $Na_2SO_3$ (600 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain the crude product. Benzoic acid was obtained in 94% yield without the need for further purification.

EXAMPLE 13

This example shows the oxidation of Methyl cinnamate using Condition A.

Methyl cinnamate (100 mg) was dissolved in DMF (5 mL), and $OsO_4$ (0.076 mL, 2.5% in tBuOH) was added and stirred for 5 min. OXONE (1.52 g) was added in one portion and the reaction had a final volume (7 mL). The reaction was stirred at room temperature for 3 hours or until the solution becomes colorless. This usually marks the completion of the reaction which was verified by TLC or GC. $Na_2SO_3$ (600 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain the crude product. Benzoic acid was obtained in 94% yield without the need for further purification.

EXAMPLE 14

This example shows the oxidation of cyclohexene using Condition A.

Cyclohexene (100 mg) was dissolved in DMF (10 mL), and $OsO_4$ (0.15 mL, 2.5% in tBuOH) was added and stirred for 5 min. OXONE (2.95 g) was added in one portion and the reaction had a final volume (14 mL). The reaction was stirred at room temperature for 3 hours or until the solution becomes colorless. This usually marks the completion of the reaction which was verified by TLC or GC. $Na_2SO_3$ (600 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain the crude product. Adipic acid was obtained in 50% yield, 94% yield by GC, after purification by silica gel column chromatography.

EXAMPLE 15

This example shows the oxidation of cyclooctene using Condition A.

Cyclooctene (100 mg) was dissolved in DMF (10 mL), and $OsO_4$ (0.11 mL, 2.5% in tBuOH) was added and stirred for 5 min. OXONE (2.23 g) was added in one portion and the reaction had a final volume (14 mL). The reaction was stirred at room temperature for 3 hours or until the solution becomes colorless. This usually marks the completion of the reaction which was verified by TLC or GC. $Na_2SO_3$ (600 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain the crude product. Suberic acid was obtained in 82% yield, 92% yield by GC, after purification by silica gel column chromatography.

EXAMPLE 16

This example shows the oxidation of 1-decene using Condition A.

1-Decene (100 mg) was dissolved in DMF (6 mL), and $OsO_4$ (0.088 mL, 2.5% in tBuOH) was added and stirred for 5 min. OXONE (1.75 g) was added in one portion and the reaction had a final volume (8 mL). The reaction was stirred at room temperature for 3 hours or until the solution becomes colorless. This usually marks the completion of the reaction which was verified by TLC or GC. $Na_2SO_3$ (600 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain the crude product. Nonanoic acid was obtained in 93% yield without the need for further purification.

EXAMPLE 17

This example shows the oxidation of 1-nonene using Condition A.

1-Nonene (100 mg) was dissolved in DMF (5 mL), and $OsO_4$ (0.1 mL, 2.5% in tBuOH) was added and stirred for 5 min. OXONE (1.94 g) was added in one portion and the reaction had a final volume (7 mL). The reaction was stirred at room temperature for 3 hours or until the solution becomes colorless. This usually marks the completion of the reaction which was verified by TLC or GC. $Na_2SO_3$ (600 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain the crude product. Octanoic acid was obtained in 90% yield without the need for further purification.

EXAMPLE 18

This example shows the oxidation of 2-trans-nonene using Condition A.

2-trans-Nonene (100 mg) was dissolved in DMF (5 mL), and $OsO_4$ (0.1 mL, 2.5% in tBuOH) was added and stirred for 5 min. OXONE (1.94 g) was added in one portion and the reaction had a final volume (7 mL). The reaction was stirred at room temperature for 3 hours or until the solution becomes colorless. This usually marks the completion of the reaction which was verified by TLC or GC. $Na_2SO_3$ (600 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain the crude product. Heptanoic acid was obtained in 93% yield without the need for further purification.

EXAMPLE 19

This example shows the oxidation of methyl oleate using Condition A.

Methyl oleate (50 mg) was dissolved in DMF (2 mL), and $OsO_4$ (0.02 mL, 2.5% in tBuOH) was added and stirred for 5 min. OXONE (0.418 g) was added in one portion and the reaction had a final volume (2.5 mL). The reaction was stirred at room temperature for 3 hours or until the solution becomes colorless. This usually marks the completion of the reaction which was verified by TLC or GC. $Na_2SO_3$ (300 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (20 mL×3) and brine (20 mL), dried over $Na_2SO4$, and the solvent was removed under reduced pressure to obtain the crude product. Nonanoic acid and nonanedoic acid monomethyl ester were obtained in 80% yield, 93% yield by GC, after purification by silica gel column chromatography.

EXAMPLE 20

This example shows the oxidation of 9-decenyl acetate using Condition A.[3]

9-Decenyl acetate (100 mg) was dissolved in DMF (10 mL), and $OsO_4$ (0.06 mL, 2.5% in tBuOH) was added and stirred for 5 min. OXONE (1.23 g) was added in one portion and the reaction had a final volume (12 mL). The reaction was stirred at room temperature for 3 hours or until the solution becomes colorless. This usually marks the completion of the reaction which was verified by TLC or GC. $Na_2SO_3$ (600 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain the crude product. 9-Acetoxy nonanoic acid was obtained in 93% yield without the need for further purification.

EXAMPLE 21

This example shows the oxidation of (−)-isopulegol using Condition A.

(−)-Isopulegol (60 mg) was dissolved in DMF (4 mL), and $OsO_4$ (0.05 mL, 2.5% in tBuOH) was added and stirred for 5 min. OXONE (0.235 g) was added in one portion and the reaction had a final volume (6 mL). The reaction was stirred at room temperature for 3 hours or until the solution becomes colorless. This usually marks the completion of the reaction which was verified by TLC or GC. $Na_2SO_3$ (360 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain the crude product. (1R, 2R, 5R)-2-Acetyl-5-methyl cyclohexanol and (1R, 2R, 5R)-2-Acetyl-5-methyl cyclohexanyl formate were obtained in 44% and 34% yield respectively after purification by silica gel column chromatography.

EXAMPLE 22

This example shows the oxidation of (1r, 2s, 5r)-(2-isoprenyl-5-methyl-cyclohexyl) benzyl ether using Condition A.

(1R, 2S, 5R)-(2-Isoprenyl-5-methyl-cyclohexyl) benzyl ether (120 mg) was dissolved in DMF (5 mL), and $OsO_4$ (0.18 ML, 0.13M in toluene) was added and stirred for 5 min. OXONE (1.21 g) was added in one portion and the reaction had a final volume (7 mL). The reaction was stirred at room temperature for 3 hours or until the solution becomes colorless. This usually marks the completion of the reaction which was verified by TLC or GC. $Na_2SO_3$ (720 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain the crude product. (1R, 2R, 5R)-(2-Acetyl-5-methylcyclohexyl) benzyl ether was obtained in 80% yield after purification by silica gel column chromatography.

EXAMPLE 23

This example shows the oxidation of 4,4-dimethyl stilbene using Condition A.

4,4'-Dimethyl stilbene (10 mg) was dissolved in DMF (1 mL), and $OsO_4$ (0.006 mL, 2.5% in tBuOH) was added and stirred for 5 min. OXONE (0.118 g) was added in one portion and the reaction had a final volume (1.2 mL). The reaction was stirred at room temperature for 3 hours or until the solution becomes colorless. This usually marks the completion of the reaction which was verified by TLC or GC. $Na_2SO_3$ (60 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (10 mL×3) and brine (10 mL), dried over $Na_2SO_4$, and the solvent was removed under reduced pressure to obtain the crude product. 4-Methyl benzoic acid was obtained in 95% yield without the need for further purification.

EXAMPLE 24

This example shows the oxidation of 4,4'-dinitro stilbene using Condition A.

4,4'-Dinitro stilbene (13 mg) was dissolved in DMF (1 mL), and $OsO_4$ (0.006 mL, 2.5% in LBuOH) was added and stirred for 5 min. OXONE (0.118 g) was added in one portion and the reaction had a final volume (1.2 mL). The reaction was stirred at room temperature for 3 hours or until the solution becomes colorless. This usually marks the completion of the reaction which was verified by TLC or GC. $Na_2SO_3$ (78 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (10 mL×3) and brine (10 mL), dried over $Na_2SO_4$, and the solvent was removed under reduced pressure to obtain the crude product. 4-Nitro benzoic acid was obtained in 91% yield after purification by silica gel column chromatography.

EXAMPLE 25

This example shows the oxidation of 2-cyclohexeneone using Condition A.

2-Cyclohexeneone (100 mg) was dissolved in DMF (10 mL), and $OsO_4$ (0.12 mL, 2.5% in tBuOH) was added and stirred for 5 min. OXONE (2.56 g) was added in one portion and the reaction had a final volume (12 mL). The reaction was stirred at room temperature for 3 hours or until the solution becomes colorless. This usually marks the completion of the reaction which was verified by TLC or GC. $Na_2SO_3$ (600 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain the crude product. Glutaric acid was obtained in 92% GC yield. This product was not isolated.

EXAMPLE 26

This example shows the oxidation of α-methyl cinnamic acid using Condition B.

The α-Methyl cinnamic acid (100 mg) was dissolved in DMF (5 mL), and $OsO_4$ (0.076 mL, 2.5% in tBuOH) was added and stirred for 5 min. A solid mixture of OXONE (1.52 g) and $NaHCO_3$ (0.206 g) was added in one portion and the reaction had a final volume (7 mL). The reaction was stirred at room temperature for 3 hours or until the solution becomes colorless. This usually marks the completion of the reaction which was verified by TLC or GC. $Na_2SO_3$ (600 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain the crude product. Benzoic acid was obtained in 82% yield, 90% yield by GC, without the need for further purification.

EXAMPLE 27

This example shows the oxidation of methyl cyclohexene using Condition B.

Methyl cyclohexene (100 mg) was dissolved in DMF (5 mL), and $OsO_4$ (0.13 mL, 2.5% in tBuOH) was added and stirred for 5 min. A solid mixture of OXONE (2.53 g) and $NaHCO_3$ (0.346 g) was added in one portion and the reaction had a final volume (8 mL). The reaction was stirred at room temperature for 3 hours or until the solution becomes colorless. This usually marks the completion of the reaction which was verified by TLC or GC. $Na_2SO_3$ (600 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain the crude product. 6-Oxyheptanoic acid was obtained in 80% yield, 85% yield by GC, after purification by silica gel column chromatography.

EXAMPLE 28

This example shows the oxidation of 2,3-diphenyl-2-butene using Condition B.

2,3-Diphenyl-2-butene (10 mg) was dissolved in DMF (1 mL), and $OsO_4$ (0.13 mL, 2.5% in tBuOH) was added and stirred for 5 min. A solid mixture of OXONE (0.118 g) and $NaHCO_3$ (0.016 g) was added in one portion and the reaction had a final volume (1.3 mL). The reaction was stirred at room temperature for 3 hours or until the solution becomes colorless. This usually marks the completion of the reaction which was verified by TLC or GC. $Na_2SO_3$ (60 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (10 mL×3) and brine (10 mL), dried over $Na_2SO_4$, and the solvent was removed under reduced pressure to obtain the crude product. Acetophenone was obtained in 85% yield after purification by silica gel column chromatography.

EXAMPLE 29

This example shows the oxidation of (+)-pulegone using Condition B.

(+)-Pulegone (500 mg) was dissolved in DMF (25 mL), and $OsO_4$ (0.41 mL, 2.5% in tBuOH) was added and stirred for 5 min. A solid mixture of OXONE (8.06 g) and $NaHCO_3$ (1.10 g) was added in one portion and the reaction had a final volume (30 mL). The reaction was stirred at room temperature for 3 hours or until the solution becomes colorless. This usually marks the completion of the reaction which was verified by TLC or GC. $Na_2SO_3$ (3.0 g) was added, to reduce the remaining Os(VIII), and stirred for an additional hour or until solution became dark brown/black. EtOAc was added to extract the products and 1N HCl was used to dissolve the salts. The organic extract was washed with 1N HCl (100 mL×3) and brine (100 mL), dried over $Na_2SO_4$, and the solvent was removed under reduced pressure to obtain the crude product. 3R-Methyladipic acid was obtained in 67% yield after purification by silica gel column chromatography.

EXAMPLE 30

This example shows the oxidation of Nootkatone using Condition A.

Nootkatone (250 mg) was dissolved in DMF (15 mL), and $OsO_4$ (0.14 mL, 2.5% in tBuOH) was added and stirred for 5 min. OXONE (1.40 g) was added in one portion and the reaction had a final volume (18 mL). The reaction was stirred at room temperature for 3 hours or until the solution becomes colorless. This usually marks the completion of the reaction which was verified by TLC or GC. $Na_2SO_3$ (3.0 g) was added, to reduce the remaining Os(VIII), and stirred for an additional hour or until solution became dark brown/black. EtOAc was added to extract the products and 1N HCl was used to dissolve the salts. The organic extract was washed with 1N HCl (100 mL×3) and brine (100 mL), dried over $Na_2SO_4$, and the solvent was removed under reduced pressure to obtain the crude product. (4S, 4aR, 6R)-6-Acetyl-4,4a-dimethyl-4,4a,5,6,7,8-hexahydro-3H-naphthalen-2-one was obtained in 60% yield after purification by silica gel column chromatography.

EXAMPLE 31

This example shows the oxidation of 15-hexadecynyl acetate using Condition A.

15-Hexadecynyl acetate (50 mg) was dissolved in DMF (2 mL), and $OsO_4$ (0.14 mL, 2.5% in tBuOH) was added and stirred for 5 min. OXONE (0.438 g) was added in one portion and the reaction had a final volume (3 mL). The reaction was stirred at room temperature for 24 hours and $Na_2SO_3$ (300 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (10 mL×3) and brine (10 mL), dried over $Na_2SO_4$, and the solvent was removed under reduced pressure to obtain the crude product. Starting material was obtained in 96% yield after purification by silica gel column chromatography.

EXAMPLE 32

This example shows the preparation of benzoic acid from trans-stilbene using $K_2OsO_4*2H_2O$ under Condition C.

trans-Stilbene (100 mg) was dissolved in DMF (5 mL), and $K_2OsO_4*2H_2O$ (0.4 mg) was added and stirred for 5 min. OXONE (1.23 g) was added in one portion and the reaction had a final volume (7 mL). The reaction was stirred at room temperature for 3 hours or until the solution becomes colorless. This usually marks the completion of the reaction which was verified by TLC or GC. $Na_2SO_3$ (540 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (30 mL×3) and brine(30 mL), dried over Na$_2$SO$_4$, and the solvent was removed under reduced pressure to obtain the crude product. Benzoic acid was obtained in 95% yield without the need for further purification.

EXAMPLE 33

This example shows the preparation of benzoic acid using polymer supported OsO$_4$ trans-stilbene using Condition D.

trans-Stilbene (50 mg) was dissolved in DMF (2 mL), and OsO$_4$ (355 mg, 1 wt % on poly(4-vinylpyridine)) was added and stirred for 5 min. OXONE (0.683 g) was added in one portion and the reaction had a final volume (2.5 mL). The reaction was stirred at room temperature for 3 hours or until the solution becomes colorless. This usually marks the completion of the reaction which was verified by TLC or GC. The reaction was filtered and washed with EtOAc. The organic filtrate was washed with 1N HCl (30 mL×3) and brine(30 mL), dried over Na$_2$SO$_4$, and the solvent was removed under reduced pressure to obtain the crude product. Benzoic acid was obtained in 96% yield without the need for further purification.

EXAMPLE 34

This example shows the large-scale preparation of benzoic acid from trans-stilbene using Condition E.

trans-Stilbene (9 g) was dissolved in DMF (250 mL), and OsO$_4$ (0.2 mL, 2.5% in tBuOH, 0.0002 eq) was added and stirred for five minutes. OXONE (123 g) was then added slowly via a solid addition funnel over 2 hours. The reaction was stirred at room temperature for 6 hours followed by addition of Na$_2$SO$_3$ (54 g) and stirred for an additional hour. The reaction was diluted with Et$_2$O (750 mL) and stirred for 10 min. The solid was filtered off and washed with Et$_2$O (75 mL×3). The organic extract is washed with 1N HCl (200 mL×3) and brine (200 mL) and dried over Na$_2$SO$_4$. The solvent was removed under reduced pressure to obtain the product at 11.60 g and 95% yield. The final product was crystallized from hot chloroform to obtain benzoic acid (10.74 g, 88%).

EXAMPLE 35

This example shows preparation of an aldehyde from trans-stilbene using Condition F.

trans-Stilbene (100 mg, 1 eq) was dissolved in freshly distilled CH$_2$Cl$_2$ (5 mL, 0.1 M), and OsO$_4$ (0.076 mL, 2.5% in tBuOH, 0.01 eq) was added and stirred for 5 min. Tetrabutylammoniumperoxysulfate (450 mg, 90% pure, 2 eq) was added in one portion and the reaction had a final volume (6 mL). The reaction was stirred at room temperature for 3 hours or until the solution becomes colorless. This usually marks the completion of the reaction which was verified by TLC. Na$_2$SO$_3$ (600 mg, 6 eq w/w) was added, to reduce the remaining Os(VIII), and stirred for an additional hour or until solution became dark brown/black. The solvent was removed under reduced pressure to obtain the crude product which was chromatographed on silica gel using 0–5% MeOH/CH$_2$Cl$_2$. Benzaldehyde was obtained in 55% yield along with benzoic acid in 20% yield.

EXAMPLE 36

This example shows preparation of an aldehyde from trans-stilbene using Condition G.

trans-Stilbene (100 mg, 1 eq) was dissolved in freshly distilled CH$_2$Cl$_2$ (5 mL, 0.1M), and OsO$_4$ (0.38 mL, 2.5% in tBuOH, 0.05 eq) was added and stirred for 5 min. OXONE (676 mg, 2 eq) was added in one portion and the reaction had a final volume (7 mL). The reaction was stirred at room temperature and monitored by GC for 36 hours. Na$_2$SO$_3$ (600 mg, 6 eq w/w) was added, to reduce the remaining Os(VIII), and stirred for an additional hour or until solution became dark brown/black. The solvent was removed under reduced pressure to obtain the crude product which was chromatographed on silica gel providing benzaldehyde 92% yield.

EXAMPLE 37

This example shows the preparation of the ester methyl benzoate from trans-stilbene using Condition H.

trans-Stilbene (100 mg) was dissolved in MeOH (5 mL), and OsO$_4$ (0.076 mL, 2.5% in tBuOH) was added and stirred for 5 min. OXONE (1.35 g) was added in one portion and the reaction had a final volume (7 mL). The reaction was stirred at room temperature for 18 hours or until the solution becomes colorless. This usually marks the completion of the reaction which was verified by TLC or GC. Na$_2$SO$_3$ (540 mg) was added, to reduce the remaining Os(VIII), and stirred for an additional hour or until solution became dark brown/black. The solvent was removed under reduced pressure and EtOAc was then added to extract the products and 1N HCl was used to dissolve the salts. The organic extract was washed with 1N HCl (30 mL×3) and brine (30 mL), dried over Na$_2$SO$_4$, and the solvent was removed under reduced pressure to obtain the crude product. Methyl benzoate was obtained in 94% yield without the need for further purification.

EXAMPLE 38

This example shows the Preparation of the ester methyl benzoate from styrene using Condition H.

Styrene (100 mg) was dissolved in MeOH (10 mL)), and OsO$_4$ (0.12 mL, 2.5% in tBuOH) was added and stirred for 5 min. OXONE (2.36 g) was added in one portion and the reaction had a final volume (13 mL). The reaction was stirred at room temperature for 18 hours or until the solution becomes colorless. This usually marks the completion of the reaction which was verified by TLC or GC. Na$_2$SO$_3$ (600 mg) was added, to reduce the remaining Os(VIII), and stirred for an additional hour or until solution became dark brown/black. The solvent was removed under reduced pressure and EtOAc was then added to extract the products and 1N HCl was used to dissolve the salts. The organic extract was washed with 1N HCl (50 mL×3) and brine(50 mL), dried over Na$_2$SO$_4$, and the solvent was removed under reduced pressure to obtain the crude product. Methyl benzoate was obtained in 72% yield without the need for further purification.

EXAMPLE 39

This example shows the preparation of the ester of methyl 9-acetoxy nonanoate from 9-decenyl acetate using Condition H.

9-Decenyl acetate (100 mg) was dissolved in MeOH (10 mL), and OsO$_4$ (0.06 mL, 2.5% in tBuOH) was added and stirred for 5 min. OXONE (1.23 g) was added in one portion and the reaction had a final volume (12 mL). The reaction was stirred at room temperature for 18 hours or until the solution becomes colorless. This usually marks the completion of the reaction which was verified by TLC or GC. Na$_2$SO$_3$ (600 mg) was added, to reduce the remaining Os(VIII), and stirred for an additional hour or until solution became dark brown/black. The solvent was removed under reduced pressure and EtOAc was then added to extract the products and 1N HCl was used to dissolve the salts. The organic extract was washed with 1N HCl (50 mL×3) and brine (50 mL), dried over $Na_2SO_4$, and the solvent was removed under reduced pressure to obtain the crude product. Methyl 9-acetoxy nonanoate was obtained in 68% yield after purification by silica gel column chromatography.

EXAMPLE 40

This example shows the preparation of the ester suberic acid dimethyl ester from cyclooctene using Condition H.

Cyclooctene (100 mg) was dissolved in MeOH (10 mL), and $OsO_4$ (0.11 mL, 2.5% in tBuOH) was added and stirred for 5 min. OXONE (2.23 g) was added in one portion and the reaction had a final volume (14 mL). The reaction was stirred at room temperature for 18 hours or until the solution becomes colorless. This usually marks the completion of the reaction which was verified by TLC or GC. $Na_2SO_3$ (600 mg) was added, to reduce the remaining Os(VIII), and stirred for an additional hour or until solution became dark brown/black. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain the crude product. Suberic acid dimethyl ester was obtained in 30% yield after purification by silica gel column chromatography.

EXAMPLE 41

This example shows the preparation of a macrocycle lactone from an olefin using Condition A.

The olefin (6 mg) was dissolved in $d_7$-DMF (1 mL), and $OsO_4$ (0.002 mL, 2.5% in tBuOH) was added and stirred for 5 min. OXONE (45 mg) was added in one portion and the reaction was stirred at room temperature for 45 min. The completion of the reaction was verified by TLC and $^1H$ NMR. $Na_2SO_3$ (6 eq w/w) was added, to reduce the remaining Os(VIII), and stirred for an additional hour or until solution became dark brown/black. EtOAc was added to extract the products and 1N HCl was used to dissolve the salts. The organic extract was washed with 1N HCl (3×) and brine, dried over $Na_2SO_4$, and the solvent was removed under reduced pressure to obtain the crude product. Product was purified by silica gel column chromatography to obtain the desired lactone in 96% yield.

EXAMPLE 42

This example shows the preparation of esters from benzaldehyde in interactive solvents using Condition I.

To prepare methyl benzoate, benzaldehyde (200 mg) was dissolved in MeOH (20 mL), and OXONE (1.16 g) was added and stirred at room temperature for 18 hours with the reaction having a final volume (21 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain methyl benzoate in 96% yield without the need for further purification.

To prepare ethyl benzoate, benzaldehyde (200 mg) was dissolved in EtOH (20 mL), and OXONE (1.16 g) was added and stirred at room temperature for 18 hours with the reaction having a final volume (21 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain ethyl benzoate in 90% yield without the need for further purification.

To prepare n-propyl benzoate, benzaldehyde (200 mg) was dissolved in nPrOH (20 mL), and OXONE (1.16 g) was added and stirred at room temperature for 18 hours with the reaction having a final volume (21 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain n-propyl benzoate in 94% yield without the need for further purification.

To prepare isopropyl benzoate, benzaldehyde (200 mg) was dissolved in iPrOH (20 mL), and OXONE (1.16 g) was added and stirred at room temperature for 18 hours with the reaction having a final volume (21 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain isopropyl benzoate in 95% yield without the need for further purification.

To prepare benzoic acid, benzaldehyde (200 mg) was dissolved in tBuOH (20 mL), and OXONE (1.16 g) was added and stirred at room temperature for 48 hours with the reaction having a final volume (21 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain benzoic acid in 99% yield without the need for further purification.

To prepare methyl hexanoate, hexanal (1 g) was dissolved in MeOH (20 mL), and OXONE (6.13 g) was added and stirred at room temperature for 18 hours with the reaction having a final volume (26 mL). The reaction was monitored by TLC or GC analysis. EtOAc was added to extract the products and 1N HCl was used to dissolve the salts. The organic extract was washed with 1N HCl (100 mL×3) and brine (100 mL), dried over $Na_2SO_4$, and the solvent was removed under reduced pressure to obtain methyl hexanoate in 93% yield without the need for further purification.

To prepare ethyl hexanoate, hexanal (50 mg) was dissolved in EtOH (3 mL), and OXONE (0.308 g) was added and stirred at room temperature for 18 hours with the reaction having a final volume (4 mL). The reaction was monitored by TLC or GC analysis. EtOAc was added to extract the products and 1N HCl was used to dissolve the salts. The organic extract was washed with 1N HCl (10 mL×3) and brine (10 mL)), dried over $Na_2SO_4$, and the solvent was removed under reduced pressure to obtain ethyl hexanoate in 95% yield without the need for further purification.

To prepare isopropyl hexanoate, hexanal (50 mg) was dissolved in iPrOH (3 mL), and OXONE (0.308 g) was added and stirred at room temperature for 18 hours with the reaction having a final volume (4 mL). The reaction was monitored by TLC or GC analysis. EtOAc was added to extract the products and 1N HCl was used to dissolve the salts. The organic extract was washed with 1N HCl (10 mL×3) and brine (10 mL), dried over $Na_2SO_4$, and the solvent was removed under reduced pressure to obtain isopropyl hexanoate in 90% yield without the need for further purification.

To prepare hexanoic acid, hexanal (1 g) was dissolved in tBuOH (20 mL), and OXONE (6.13 g) was added and stirred at room temperature for 36 hours with the reaction having a final volume (26 mL). The reaction was monitored by TLC or GC analysis. EtOAc was added to extract the products and 1N HCl was used to dissolve the salts. The organic extract was washed with 1N HCl (100 mL×3) and brine (100 mL), dried over $Na_2SO_4$, and the solvent was removed under reduced pressure to obtain hexanoic acid in 90% yield without the need for further purification.

To prepare methyl nonanoate, nonanal (1 g) was dissolved in MeOH (20 mL), and OXONE (4.32 g) was added and stirred at room temperature for 18 hours with the reaction having a final volume (24 mL). The reaction was monitored by TLC or GC analysis. EtOAc was added to extract the products and 1N HCl was used to dissolve the salts. The organic extract was washed with 1N HCl (100 mL×3) and brine (100 mL), dried over $Na_2SO_4$, and the solvent was removed under reduced pressure to obtain methyl nonanoate in 92% yield without the need for further purification.

To prepare methyl cyclohexanoate, cyclohexanal (1 g) was dissolved in MeOH (20 mL), and OXONE (5.49 g) was added and stirred at room temperature for 18 hours with the reaction having a final volume (25 mL). The reaction was monitored by TLC or GC analysis. EtOAc was added to extract the products and 1N HCl was used to dissolve the salts. The organic extract was washed with 1N HCl (100 mL×3) and brine (100 mL), dried over $Na_2SO_4$, and the solvent was removed under reduced pressure to obtain methyl cyclohexanoate in 83% yield without the need for further purification.

To prepare methyl 3-methyl sulfonepropanoate, 3-thiomethyl propanal (0.25 g) was dissolved in MeOH (10 mL), and OXONE (5.90 g) was added and stirred at room temperature for 18 hours with the reaction having a final volume (15 mL). The reaction was monitored by TLC or GC analysis. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain methyl 3-methyl sulfonepropanoate in 38% yield after purification by silica gel column chromatography. 1H NMR ($CDCl_3$, 300 MHz): δ3.68 (s, 3H), 3.32 (t, 2H, J=7.4), 2.91 (s, 3H), 2.84 (t, 2H, J=7.4).m/z=167 m+H.

To prepare 6-ethyl-4-hydroxy-2-methoxy-4a,8a-dihydro-2H-chromene-3-carboxylic acid methyl ester, 6-ethyl-3-formyl chromone (0.25 g) was dissolved in MeOH (10 mL), and OXONE (0.76 g) was added and stirred at room temperature for 18 hours with the reaction having a final volume (13 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain 6-ethyl-4-hydroxy-2-methoxy-4a,8a-dihydro-2H-chromene-3-carboxylic acid methyl ester in 45% yield after purification by silica gel column chromatography. $^1$H NMR ($CDCl_3$, 300 MHz): δ7.68 (d, 1H, J=2.3), 7.40 (dd, 1H, J=2.2, 8.6), 6.99 (d, 1H, J=8.3), 5.08 (s, 1H), 3.72 (s, 3H), 3.69 (s, 3H), 2.60 (q, 2H,J=7.6), 1.20 (t, 3H, J=7.7); $^{13}$C NMR ($CDCl_3$, 75 MHz): δ188.9, 167.4, 156.7, 138.4, 137.5, 126.1, 118.8, 104.6, 78.6, 58.3, 53.6, 27.8, 15.2.

To prepare methyl 4-oxy-4-(4-bromophenyl) butanoate, 5-(4-bromophenyl)-2-furaldehyde (0.25 g) was dissolved in MeOH (10 mL), and OXONE (0.61 g) was added and stirred at room temperature for 18 hours with the reaction having a final volume (12 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain methyl 4-oxy-4-(4-bromophenyl) butanoate in 75% yield after purification by silica gel column chromatography. $^1$H NMR ($CDCl_3$, 300 MHz): δ7.80 (d, 2H, J=2.2), 7.77 (d, 2H, J=2.0), 3.65 (s, 3H), 3.22 (t, 2H,J=6.6), 2.49 (t, 2H,-J=6.6); $^{13}$C NMR ($CDCl_3$, 75 MHz): δ197.0, 173.2, 135.1, 131.9, 129.5, 128.4, 51.8, 33.2, 27.8.

To prepare methyl 4-methylbenzoate, 4-methylbenzaldehyde (50 mg) was dissolved in MeOH (5 mL), and OXONE (0.256 g) was added and stirred at room temperature for 18 hours with the reaction having a final volume (6 mL). The reaction was monitored by TLC or GC analysis. EtOAc was added to extract the products and 1N HCl was used to dissolve the salts. The organic extract was washed with 1N HCl (20 mL×3) and brine (20 mL), dried over $Na_2SO_4$, and the solvent was removed under reduced pressure to obtain methyl 4-methylbenzoate in 94% yield without the need for further purification.

To prepare methyl 4-chlorobenzoate, 4-chlorobenzaldehyde (100 mg) was dissolved in MeOH (10 mL), and OXONE (0.437 g) was added and stirred at room temperature for 18 hours with the reaction having a final volume (11 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain methyl 4-chlorobenzoate in 98% yield without the need for further purification.

To prepare methyl 4-methoxybenzoate, 4-methoxybenzaldehyde (100 mg) was dissolved in MeOH (10 mL), and OXONE (0.451 g) was added and stirred at room temperature for 18 hours with the reaction having a final volume (11 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain methyl 4-methoxybenzoate in 19% yield and 4-methoxy phenol in 77% yield after purification by silica gel column chromatography.

To prepare methyl 4-hydroxybenzoate, 4-hydroxybenzaldehyde (100 mg) was dissolved in MeOH (10 mL), and OXONE (0.503 g) was added and stirred at room temperature for 18 hours with the reaction having a final volume (11 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain methyl 4-hydroxybenzoate in 4% yield and 4-hydroxyphenol in 77% yield after purification by silica gel column chromatography.

To prepare methyl 4-nitrobenzoate, 4-nitrobenzaldehyde (100 mg) was dissolved in MeOH (10 mL), and OXONE (1.16 g) was added. The reaction was heated to reflux and stirred for 18 hours with the reaction having a final volume (11 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain methyl 4-nitrobenzoate in 98% yield without the need for further purification.

To prepare methyl 4-cyanobenzoate, 4-cyanobenzaldehyde (100 mg) was dissolved in MeOH (10 mL), and OXONE (0.469 g) was added. The reaction was heated to reflux and stirred for 18 hours with the reaction having a final volume (11 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain methyl 4-cyanobenzoate in 98% yield without the need for further purification.

EXAMPLE 43

This example shows the preparation of benzoic derivatives from various benzaldehydes using Condition J.

To prepare benzoic acid, benzaldehyde (1 g) was dissolved in DMF (10 mL), and OXONE (5.79 g) was added and stirred at room temperature for 3 hours with the reaction having a final volume (13 mL). The reaction was monitored by TLC or GC analysis. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain benzoic acid in 97% yield without the need for further purification.

To prepare 4-methylbenzoic acid, 4-methylbenzaldehyde (1 g) was dissolved in DMF (10 mL), and OXONE (5.17 g) was added and stirred at room temperature for 3 hours with the reaction having a final volume (13 mL). The reaction was monitored by TLC or GC analysis. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain 4-methylbenzoic acid in 97% yield without the need for further purification.

To prepare 4-chlorobenzoic acid, 4-chlorobenzaldehyde (1 g) was dissolved in DMF (10 mL), and OXONE (4.37 g) was added and stirred at room temperature for 3 hours with the reaction having a final volume (13 mL). The reaction was monitored by TLC or GC analysis. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain 4-chlorobenzoic acid in 97% yield without the need for further purification.

To prepare 4-methoxybenzoic acid, 4-methoxybenzaldehyde (100 mg) was dissolved in DMF (10 mL), and OXONE (0.451 g) was added and stirred at room temperature for 3 hours with the reaction having a final volume (11 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain 4-methoxybenzoic acid in 31% yield and 4-methoxyphenol formate in 58% yield after purification by silica gel column chromatography. 4-Methoxyphenyl Formate: 1H NMR ($CDCl_3$, 300 MHz): δ8.26 (s, 1H), 7.03 (d, 2H, J=9.0), 6.89 (d, 2H,J=8.9), 3.78 (s, 3H); $^{13}$C NMR ($CDCl_3$, 75 MHz): 8176.7, 170.5, 79.9, 74.3, 31.4, 30.4, 28.2, 24.8, 23.9, 22.4, 20.9, 13.9.

To prepare 4-hydroxy benzoic acid, 4-hydroxybenzaldehyde (100 mg) was dissolved in DMF (10 mL), and OXONE (0.503 g) was added and stirred at room temperature for 18 hours with the reaction having a final volume (11 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain 4-hydroxy benzoic acid in 19% yield and 4-hydroxyphenol formate in 62% yield after purification by silica gel column chromatography. 4-Hydroxyphenyl Formate: 1H NMR ($CDCl_3$, 300 MHz): δ8.27 (s, 1H), 6.98(d, 2H, J=9.0), 6.78 (d, 2H,J=8.9), 5.35 (bs, 1H).

To prepare 4-nitrobenzoic acid, 4-nitrobenzaldehyde (250 mg) was dissolved in DMF (10 mL), and OXONE (1.01 g) was added and stirred at room temperature for 3 hours with the reaction having a final volume (12 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain 4-nitrobenzoic acid in 95% yield without the need for further purification.

To prepare 4-cyanobenzoic acid, 4-cyanobenzaldehyde (500 mg) was dissolved in DMF (10 mL), and OXONE (2.34 g) was added and stirred at room temperature for 3 hours with the reaction having a final volume (13 mL). The reaction was monitored by TLC or GC analysis. EtOAc was added to extract the products and 1N HCl was used to dissolve the salts. The organic extract was washed with 1N HCl (40 mL×3) and brine (40 mL), dried over $Na_2SO_4$, and the solvent was removed under reduced pressure to obtain 4-cyanobenzoic acid in 85% yield without the need for further purification.

To prepare 3-bromobenzoic acid, 3-bromobenzaldehyde (200 mg) was dissolved in DMF (10 mL), and OXONE (0.665 g) was added and stirred at room temperature for 3 hours with the reaction having a final volume (11 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain 3-bromobenzoic acid in 97% yield without the need for further purification.

To prepare 2-chlorobenzoic acid, 2-chlorobenzaldehyde (1 g) was dissolved in DMF (20 mL), and OXONE (4.37 g) was added and stirred at room temperature for 3 hours with the reaction having a final volume (23 mL). The reaction was monitored by TLC or GC analysis. EtOAc was added to extract the products and 1N HCl was used to dissolve the salts. The organic extract was washed with 1N HCl (50 mL×3) and brine (50 mL), dried over $Na_2SO_4$, and the solvent was removed under reduced pressure to obtain 2-chlorobenzoic acid in 90% yield without the need for further purification.

To prepare terepthalic acid mono methyl ester, methyl 4-formyl benzoate (250 mg) was dissolved in DMF (10 mL), and OXONE (0.936 g) was added and stirred at room temperature for 3 hours with the reaction having a final volume (12 mL). The reaction was monitored by TLC or GC analysis. EtOAc was added to extract the products and 1N HCl was used to dissolve the salts. The organic extract was washed with 1N HCl (40 mL×3) and brine (40 mL), dried over $Na_2SO_4$, and the solvent was removed under reduced pressure to obtain terepthalic acid mono methyl ester in 95% yield without the need for further purification.

EXAMPLE 44

This example shows the oxidation products of various compounds using Condition J.

To prepare 6-ethyl-4-oxo-4a,8a-dihydro-4H-chromene-3-carboxylic acid, 6-ethyl-3-formyl chromone (0.25 g) was dissolved in DMF (10 mL), and OXONE (0.76 g) was added and stirred at room temperature for 3 hours with the reaction having a final volume (12 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain 6-ethyl-4-oxo-4a,8a-dihydro-4H-chromene-3-carboxylic acid in 52% yield and 6-ethyl-3-hydroxy-4a,8a-dihydro-chromene-4-one in 34% yield after purification by silica gel column chromatography.

6-ethyl-4-oxo-4a,8a-dihydro-4H-chromene-3-carboxylic acid: $^1$H NMR (CDCl$_3$, 300 MHz): δ13.50 (bs, 1H), 8.98 (s, 1H), 8.11 (s, 1H), 7.68 (dd, 1H, J=2.2, 8.5), 7.55 (d, 1H, J=8.8), 6.80 (bs, 1H), 2.72 (q, 2H, J=7.7), 1.24 (t, 3H, J=7.7). 6-ethyl-3-hydroxy-4a,8a-dihydro-chromene-4-one: $^1$H NMR (CDCl$_3$, 300 MHz): δ8.03 (d, 1H, J=2.2), 7.97 (s, 1H), 7.47 (dd, 1H, J=2.2, 8.8), 7.36 (d, 1H, J=8.8), 6.80 (bs, 1H), 2.72 (q, 2H, J=3.4), 1.24 (t, 3H, J=3.6).

To prepare 6-nitro-3-hydroxy-4a,8a-dihydro-chromene-4-one, 6-nitro-3-formyl chromone (0.25 g) was dissolved in DMF (10 mL), and OXONE (0.701g) was added and stirred at room temperature for 3 hours with the reaction having a final volume (12 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure. 6-Nitro-3-hydroxy-4a,8a-dihydro-chromene-4-one was obtained in 40% yield after purification by silica gel column chromatography. $^1$H NMR (CDCl$_3$, 300 MHz): δ9.07 (d, 1H, J=2.8), 8.50 (dd, 1H, J=2.7, 9.3), 8.22 (s, 1H), 7.66 (d, 1H, J=9.3), 3.72 (s, 3H), 3.69 (s, 3H), 2.60 (q, 2H, J=7.6), 1.20 (t, 3H, J=7.7); $^{13}$C NMR (CDCl$_3$, 75 MHz):171.3, 158.9, 152.7, 128.8, 123.7, 122.1, 120.5.

To prepare 5-(4-bromophenyl)-3H-furan-2-one, 5-(4-bromophenyl)-2-furaldehyde (0.25 g) was dissolved in DMF (10 mL), and OXONE (0.61 g) was added and stirred at room temperature for 3 hours with the reaction having a final volume (12 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain 5-(4-bromophenyl)-3H-furan-2-one in 42% yield after purification by silica gel column chromatography. $^1$H NMR (CDCl$_3$, 300 MHz): δ7.51 (d, 2H, J=?), 7.49 (d, 2H, J=2.2, 8.6), 5.78 (t, 1H, J=?), 3.49 (d, 2H, J=?); 13C NMR (CDCl$_3$, 75 MHz): δ175.4, 153.0, 131.9, 131.6, 127.2, 126.2, 123.7, 98.3, 34.7, 14.2.

To prepare hexanoic acid, hexanal (1 g) was dissolved in DMF (20 mL), and OXONE (6.13 g) was added and stirred at room temperature for 3 hours with the reaction having a final volume (26 mL). The reaction was monitored by TLC or GC analysis. EtOAc was added to extract the products and 1N HCl was used to dissolve the salts. The organic extract was washed with 1N HCl (100 mL×3) and brine (100 mL), dried over $Na_2SO_4$, and the solvent was removed under reduced pressure to obtain hexanoic acid in 97% yield without the need for further purification.

To prepare nonanoic acid, nonanal (1 g) was dissolved in DMF (20 mL), and OXONE (4.32 g) was added and stirred at room temperature for 3 hours with the reaction having a final volume (24 mL). The reaction was monitored by TLC or GC analysis. EtOAc was added to extract the products and 1N HCl was used to dissolve the salts. The organic extract was washed with 1N HCl (100 mL×3) and brine (100 mL), dried over $Na_2SO_4$, and the solvent was removed under reduced pressure to obtain nonanoic acid in 99% yield without the need for further purification.

To prepare cyclohexanoic acid, cyclohexanal (1 g) was dissolved in DMF (20 mL), and OXONE (5.49 g) was added and stirred at room temperature for 3 hours with the reaction having a final volume (25 mL). The reaction was monitored by TLC or GC analysis. EtOAc was added to extract the products and 1N HCl was used to dissolve the salts. The organic extract was washed with 1N HCl (100 mL×3) and brine (100 mL), dried over $Na_2SO_4$, and the solvent was removed under reduced pressure to obtain cyclohexanoic acid in 97% yield without the need for further purification.

To prepare isopropanoic acid, isopropanal (0.25 g) was dissolved in DMF (10 mL), and OXONE (2.13 g) was added and stirred at room temperature for 3 hours with the reaction having a final volume (13 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain isopropanoic acid in 33% yield without the need for further purification.

To prepare 1,1,1-trimethyl acetic acid, 1,1,1-trimethyl acetaldehyde (0.25 g) was dissolved in DMF (10 mL), and OXONE (1.78 g) was added and stirred at room temperature for 3 hours with the reaction having a final volume (12 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain 1,1,1-trimethyl acetic acid in 47% yield without the need for further purification.

To prepare cis-4-decenoic acid in 53% yield and 5-(1-hydroxyhexanyl)-dihydrofuran-2-one, cis-4-decenal (0.25 g) was dissolved in DMF (10 mL), and OXONE (0.995 g) was added and stirred at room temperature for 3 hours with the reaction having a final volume (25 mL). The reaction was monitored by TLC or GC analysis. EtOAc was added to extract the products and 1N HCl was used to dissolve the salts. The organic extract was washed with 1N HCl (30 mL×3) and brine (30 mL), dried over $Na_2SO_4$, and the solvent was removed under reduced pressure to obtain cis-4-decenoic acid in 53% yield and 5-(1-hydroxyhexanyl)- dihydrofuran-2-one in 32% yield after purification by silica gel column chromatography. Cis-4-decanoic acid: $^1$H NMR (CDCl$_3$, 300 MHz): δ4.36–4.42 (m, 1H), 3.50–3.56 (m, 1H), 2.49–2.62 (m, 2H), 2.05–2.27 (m, 3H), 1.49 (bs, 5H), 0.84 (bs, 3H).

To prepare 1,2,3,6-tetrahydrobenzoic acid, 1,2,3,6-tetrahydrobenzaldehyde (0.25 g) was dissolved in DMF (10 mL), and OXONE (1.40 g) was added and stirred at room temperature for 3 hours with the reaction having a final volume (12 mL). The reaction was monitored by TLC or GC analysis. EtOAc was added to extract the products and 1N HCl was used to dissolve the salts. The organic extract was washed with 1N HCl (30 mL×3) and brine (30 mL), dried over Na$_2$SO$_4$, and the solvent was removed under reduced pressure to obtain 1,2,3,6-tetrahydrobenzoic acid in 93% yield without the need for further purification. $^1$H NMR (CDCl$_3$, 300 MHz):δ 5.63–5.7 (m, 2H), 2.54–2.64 (m, 1H), 2.24–2.27 (m, 2H), 1.98–2.15 (m, 3H), 1.62–1.76 (m, 1H).

For the preceding examples, the spectral properties of 4-nitrobenzoic acid, 4-cyanobenzoic acid, 4-chlorobenzoic acid, 4-methoxycarbonylbenzoic acid, benzoic acid, 4-methylbenzoic acid, 3-bromobenzoic acid, 2-chlorobenzoic acid 4-hydroxybenzoic acid, 4-methoxybenzoic acid, hexanoic acid, nonanoic acid, cyclohexanoic acid, methyl 4-methylbenzoate, methyl 4-chlorobenzoate, methyl 4-hydroxybenzoate, methyl 4-methoxybenzoate, 4-methoxyphenol, methyl benzoate, ethyl benzoate, n-propyl benzoate, methyl hexanoate, ethyl hexanoate, methyl nonanoate, methyl cyclohexanoate, iso-propanoic acid, and 1,1,1-trimethyl acetic acid match those reported by Aldrich and comparison to authentic samples.

EXAMPLE 45

This example shows a modification of the olefin to aldehyde oxidative cleavage reaction.

In these reactions, the olefin (1 eq) was dissolved in freshly distilled DMF (0.1 M), and OsO$_4$ (0.01 eq) was added and the mixture stirred for 5 minutes. Oxone (1 eq) and KHCO$_3$ (1 eq) was added in one portion. The reaction was stirred at RT for 3 hours or until the solution became colorless. This usually marked the completion of the reaction, which was verified by GC. Na$_2$SO$_3$ (600 mg, 6 eq w/w) was added to reduce the remaining Os(VIII) and the mixture stirred for an additional hour or until the solution became dark brown/black. The reaction was then diluted with Et$_2$O and stirred for 10 minutes. The solids were filtered off and washed with Et$_2$O. The organic extract was washed with 1N HCl (3×) and brine (1×) and dried over Na$_2$SO$_4$. The solvent was removed under reduced pressure to obtain the products. The products produced from the various olefins are shown in Table 3.

TABLE 3

| Starting Material | Product | Yield (%) |
|---|---|---|
| styrene | benzaldehyde | 92 |
| trans-stilbene | benzaldehyde | 96 |
| α-methylcinnamic acid | benzaldehyde | 60 |
| cinnamic acid | benzaldehyde | 56 |
| methyl cinnamate | benzaldehyde | 94 |
| cinnamaldehyde | benzaldehyde | 80 |
| cinnamyl alcohol | benzaldehyde | 73 |
| (4-bromobut-1-enyl)benzene | benzaldehyde | 68 |
| (5-methylhex-1-enyl)benzene | benzaldehyde | 45 |
| 1,4-diphenyl-1,3-butadiene | benzaldehyde | 47 |

TABLE 3-continued

| Starting Material | Product | Yield (%) |
|---|---|---|
| 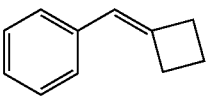 | 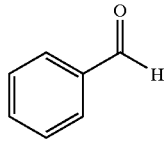 | 70 |

EXAMPLE 46

Additional examples showing the oxidative cleavage of various olefins to methyl esters are shown in Table 4.

In these reactions, the olefin (1 eq) was dissolved in MeOH (0.1 M) and $OsO_4$ (0.01 eq) was added and stirred for 5 minutes Oxone® (3eq) was added in one portion. The reaction was then stirred at RT for 18 hours or until the solution became colorless. This usually marked the completion of the reaction which was verified by TLC or GC. $Na_2SO_3$ was added to reduce the remaining Os(VIII) and the mixture stirred for an additional hour or until the solution became dark brown/black. The solvent was removed under reduced pressure and EtOAc was then added to extract the products and 1N HCl was used to dissolve the salts. The organic extract was washed with 1N HCl (3×) and brine (1×), dried over $Na_2SO_4$, and the solvent removed under reduced pressure to obtain the products as shown in Table 4.

TABLE 4

| Starting Material | Product | Yield (%) |
|---|---|---|
| 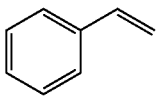 | 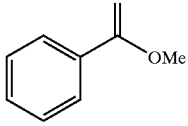 | 72 |
| 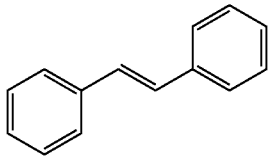 | 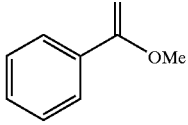 | 90 |
| 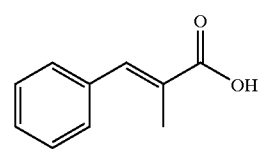 | 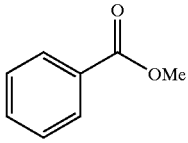 | 83 |
| 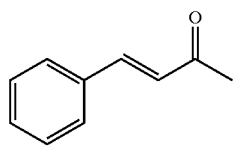 | 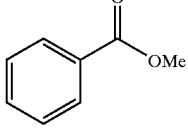 | 70 |

TABLE 4-continued

| Starting Material | Product | Yield (%) |
|---|---|---|
| 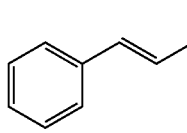 | 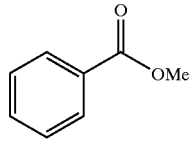 | 69 |
| 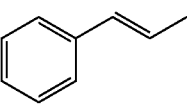 | 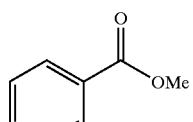 | 74 |
| 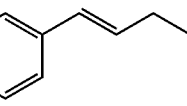 | 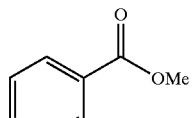 | 66 |
| 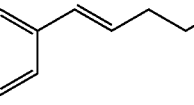 | 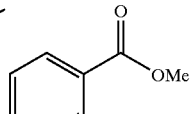 | 90 |
| 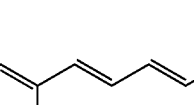 | 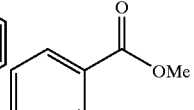 | 66 |
| 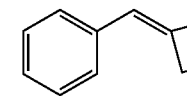 | 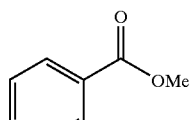 | 78 |

EXAMPLE 47

Additional examples showing the preparation of various lactones from olefins are shown in Table 5.

In these reactions, the olefin (1 eq) was dissolved in DMF (0.1M), and $OsO_4$ (0.01 eq, 2.5% in tBuOH) was added and the mixture stirred for 5 min. Oxoneo (4 eq) was added in one portion and the reaction was stirred at RT for 45 minutes. Completion of the reaction was verified by TLC and $^1H$ NMR. $Na_2SO_3$ (6 eq w/w) was added to reduce the remaining Os(VIII) and the mixture stirred for an additional hour or until solution became dark brown/black. EtOAc was added to extract the products and 1N HCl was used to dissolve the salts. The organic extract was washed with 1N HCl (3×) and brine (1×), dried over $Na_2SO_4$, and the solvent removed under reduced pressure to obtain the crude products which are shown in Table 5.

TABLE 5

| Starting Material | Product | Yield (%) |
|---|---|---|
| [alkenyl alcohol, 4 carbons + OH] | γ-butyrolactone | 73 |
| [alkenyl alcohol, 5 carbons + OH] | δ-valerolactone | 68 |
| [alkenyl alcohol, 6 carbons + OH] | ε-caprolactone | 42 |
| [gem-dimethyl alkenyl alcohol] | gem-dimethyl γ-lactone | 59 |
| [gem-dimethyl alkenyl alcohol, longer] | gem-dimethyl lactone | 85 |
| [allyl cyclohexanol] | bicyclic lactone | 82 |
| [butenyl cyclohexanol] | bicyclic 7-membered lactone | 59 |
| [butenyl cyclopentanol with OH] | spiro lactone | 73 |
| [o-vinyl benzyl-O-Si(tBu)] | phthalide | 76 |
| [divinyl biphenyl with OSi(tBu)] | dibenzo lactone | 76 |
| [cyclohexenyl ethanol] | keto-lactone | 45 |

EXAMPLE 48

Additional examples showing the preparation of acids from olefins are shown in Table 6.

In these reactions, the olefin (1 eq) was dissolved in DMF (0.1M), and $OsO_4$ (0.01 eq, 2.5% in tBuOH) was added and the mixture stirred for 5 minutes. Oxoneo (4 eq) was added in one portion and the reaction was stirred at RT for 45 minutes. Completion of the reaction was verified by TLC and $^1H$ NMR. $Na_2SO_3$ (6 eq w/w) was added to reduce the remaining Os(VIII) and the mixture stirred for an additional hour or until solution became dark brown/black. EtOAc was added to extract the products and 1N HCl was used to dissolve the salts. The organic extract was washed with 1N HCl (3×) and brine (1×), dried over $Na_2SO_4$, and the solvent removed under reduced pressure to obtain the crude products shown in Table 6.

TABLE 6

| Starting Material | Product | Yield (%) |
|---|---|---|
| [aryl allyl ether with ethanol] | [aryl acetic acid with ethoxy-ethanol] | 69 |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A process for oxidative cleavage of an oxidizable organic compound to form an oxidized organic compound which comprises:
   reacting the oxidizable organic compound with a mixture of a metal catalyst comprising osmium and a peroxy compound selected from the group consisting of peroxymonosulfuric acid and salts thereof which oxidatively cleaves the oxidizable organic compound to form the oxidized organic compound.

2. A process for oxidative cleavage of an oxidizable organic compound to form an oxidized organic compound which comprises:
   reacting the oxidizable organic compound with a mixture of a metal catalyst comprising osmium and an alkali metal monopersulfate which oxidatively cleaves the oxidizable organic compound to form the oxidized organic compound.

3. The process of claim 2 wherein the alkali metal is potassium.

4. The process of claim 1 wherein the oxidizable organic compound contains unsaturated bonds which are oxidized.

5. The process of claim 4 wherein the bonds are double bonds.

6. The process of any one of claims 1, 2, 3, 4 and 5 wherein the reaction is performed in a non-oxidizable organic solvent.

7. The process of claim 1 wherein the osmium is selected from the group consisting of osmium tetroxide ($OsO_4$), osmium trichloride ($OsCl_3$), $K_2OsO_4*2H_2O$, and mixtures thereof.

8. A process for oxidizing a carbon—carbon double bond in an organic compound to produce an organic compound selected from the group consisting of an aldehyde, ketone, carboxylic acid, and ester, comprising:
   (a) providing the organic compound with the carbon—carbon double bond in an organic solvent;
   (b) reacting the organic compound with the carbon—carbon double bond in the organic solvent with a mixture of a metal catalyst comprising osmium and an oxidizing compound selected from the group consisting of peroxymonosulfuric acid and salts thereof in a reaction wherein the carbon—carbon double bond is oxidized to produce the organic compound selected from the group consisting of an aldehyde, ketone, carboxylic acid, and ester; and
   (c) recovering the organic compound selected from the group consisting of the aldehyde, ketone, carboxylic acid, and ester from the reaction.

9. The process of claim 8 wherein the osmium is selected from the group consisting of osmium tetroxide, osmium trichioride, $K_2OsO_4*2H_2O$, and mixtures thereof.

10. The process of claim 8 or 9 wherein the metal catalyst comprising the osmium is provided in a polymer.

11. The process of claim 8 wherein the oxidizing compound is an alkali metal peroxymonosulfate.

12. The process of claim 11 wherein the alkali metal peroxymonosulfate is potassium peroxymonosulfate.

13. The process of claim 8 wherein the oxidizing compound comprises $2KHSO_5.KHSO_4.K_2SO_4$.

14. The process of claim 8 wherein the organic solvent is selected from the group consisting of dimethyl formamide, dichloromethane, methanol, ethanol, propanol, butanol, N-methyl pyrrolidinone, hexamethyl phosphonamide, pyrrolidinone, dimethyl acetomide, and acetone.

15. The process of any one of claim 8, 9, 10, 11, 12, 13, or 14 wherein the organic compound with the carbon—carbon double bond is an olefin.

16. The process of claim 15 wherein the olefin is selected from the group consisting of mono-substituted, 1,1-di-substituted, 1,2-di-substituted, tri-substituted, tetra-substituted olefins, and mixtures thereof.

17. The process of claim 8 wherein the osmium is selected from the group consisting of osmium tetroxide ($OsO_4$), osmium trichloride ($OsCl_3$), $K_2OsO_4*2H_2O$, and mixtures thereof.

18. A process for producing an ester from an aldehyde comprising:
   (a) providing the aldehyde in an alcohol as a solvent and as a reactant;
   (b) reacting the aldehyde and the alcohol in the alcohol as the solvent with an oxidizing compound selected from the group consisting of peroxymonosulfuric acid and salts thereof alone or with an additional oxidant in a reaction wherein the aldehyde is oxidized and which reacts with the alcohol solvent to form the ester; and
   (c) recovering the ester from the reaction.

19. The process of claim 18 wherein the oxidizing compound is an alkali metal peroxymonosulfate.

20. The process of claim 19 wherein the alkali metal peroxyrnonosulfate is potassium peroxymonosulfate.

21. The process of claim 19 wherein the oxidizing compound comprises $2KHSO_5.KHSO_4.K_2SO_4$.

22. The process of claim 18 wherein the alcohol solvent is a lower alcohol.

23. The process of claim 22 wherein the lower alcohol is selected from the group consisting of methanol, ethanol, propanol, and butanol.

24. A process for producing a carboxylic acid from an aldehyde comprising:
   (a) providing the aldehyde in dimethyl formamide;
   (b) reacting the aldehyde with an oxidizing compound selected from the group consisting of peroxymonosulfuric acid and salts thereof alone or with an additional oxidant in a reaction wherein the aldehyde is oxidized to the acid; and
   (c) recovering the acid from the reaction.

25. The process of claim 24 wherein the oxidizing compound is an alkali metal peroxymonosulfate.

26. The process of claim 25 wherein the alkali metal peroxymonosulfate is potassium peroxymonosulf ate.

27. The process of claim 24 wherein the oxidizing compound comprises $2KHSO_5.KHSO_4.K_2SO_4$.

* * * * *

UNITED STATES PATENT AND TRADEMARK OFFICE
CERTIFICATE OF CORRECTION

PATENT NO. : 6,787,671 B2
DATED : September 7, 2004
INVENTOR(S) : Babak Borhan, Benjamin R. Travis and Jennifer M. Schomaker It is certified that error appears in the above-- identified patent and that said Letters Patent is hereby corrected as shown below:

Column 1,
Line 66, "(KMnO4)" should be -- $(KMnO_4)$ --.

Column 2,
Line 5, "KMnO4" should be -- $KMnO_4$ --.

Column 6,
Line 7, "(OsC13)" should be -- $(OsCl_3)$ --.

Column 8,
Line 53, "olef in aldehydes" should be -- olefin aldehydes --.
Line 54, "$(C_nH_{2n}CO)$ As used" should be -- $(C_nH_{2n}CO)$. As used --.

Column 9,
Line 5, "$(K^{+13} O-S(=O)_2(-OOH)$" should be -- $(K^+ {}^-O-S(=O)_2(-OOH)$ --.

Column 13,
Lines 52 and 53, "IN HCl" should be -- 1N HCl --.

Column 14,
Line 17, "IN HCl" should be -- 1N HCl --.

Column 15,
Line 26, "$Na_2SO4$" should be -- $Na_2SO_4$ --.

Column 21,
Lines 31 and 45, "(70eV, ET)" should be -- (70eV, EI) --.
Line 40, "was 1H NMR" should be -- was $^1H$ NMR --.
Line 41, "MHz): 5 3.8" should be -- MHz): δ 3.80 --.
Line 42, "J-3.6," should be -- J=3.6, --.

Column 27,
Line 64, "4, 4-dimethyl" should be -- 4, 4´-dimethyl --.

Column 28,
Line 21, "in LBuOH)" should be -- in *t*BuOH) --.

Column 35,
Line 50, "1H NMR" should be -- $^1H$ NMR --.

Column 36,
Line 19, "MHz): 6197.0." should be -- MHz): δ197.0 --.

UNITED STATES PATENT AND TRADEMARK OFFICE
CERTIFICATE OF CORRECTION

PATENT NO. : 6,787,671 B2
DATED : September 7, 2004
INVENTOR(S) : Babak Borhan, Benjamin R. Travis and Jennifer M. Schomaker It is certified that error appears in the above-- identified patent and that said Letters Patent is hereby corrected as shown below:

Column 38,
Lines 6 and 22, "1H NMR" should be -- $^1$H NMR --.
Line 8, "MHz): 8176.7," should be -- MHz): δ176.7, --.

Column 39,
Line 56, "MHz): 171.3," should be -- MHz) : δ171.3, --.

Column 41,
Line 18, "300MHz): 6 5.63" should be -- 300MHz) :δ 5.63 --.

Column 44,
Line 57, "Oxoneo" should be -- Oxone® --.

Column 46,
Line 6, "Oxoneo" should be -- Oxone® --.
Line 66, "trichioride" should be -- trichloride --.

Column 47,
Line 20, "trichioride" should be -- trichloride --.

Column 48,
Line 17, "peroxyrnonosulfate" should be -- peroxymonosulfate --.
Line 40, "peroxymonosulf" should be -- peroxymonosulfate --.

Signed and Sealed this

Fourth Day of January, 2005

JON W. DUDAS
*Director of the United States Patent and Trademark Office*